(12) United States Patent
Eyole et al.

(10) Patent No.: US 11,803,627 B2
(45) Date of Patent: Oct. 31, 2023

(54) AUTHENTICATION SYSTEM, DEVICE AND PROCESS

(71) Applicant: Arm Limited, Cambridge (GB)

(72) Inventors: Mbou Eyole, Soham (GB); Matthew James Horsnell, Cambridge (GB)

(73) Assignee: Arm Limited, Cambridge (GB)

( * ) Notice: Subject to any disclaimer, the term of this patent is extended or adjusted under 35 U.S.C. 154(b) by 1251 days.

(21) Appl. No.: 16/271,760

(22) Filed: Feb. 8, 2019

(65) Prior Publication Data

US 2020/0257787 A1    Aug. 13, 2020

(51) Int. Cl.
| | | |
|---|---|---|
| *A61B 5/117* | (2016.01) | |
| *G06F 21/36* | (2013.01) | |
| *A61B 5/00* | (2006.01) | |
| *A61B 5/38* | (2021.01) | |
| *A61B 5/378* | (2021.01) | |

(52) U.S. Cl.
CPC ............ *G06F 21/36* (2013.01); *A61B 5/0053* (2013.01); *A61B 5/117* (2013.01); *A61B 5/378* (2021.01); *A61B 5/38* (2021.01); *A61B 5/7264* (2013.01)

(58) Field of Classification Search
CPC ............ A61N 1/36034; A61N 1/36082; A61N 1/36092; A61N 1/36132; A61N 1/3603; A61B 5/375; A61B 5/4836; A61B 5/6803; A61B 5/377; A61B 5/378; A61B 5/369; A61B 5/38; A61B 5/24; A61B 5/4088; A61B 5/291; A61B 5/0006; A61B 5/742; A61B 5/0245; A61B 5/02438; A61B 5/316; A61B 5/6821; A61B 5/0053; A61B 5/117; A61B 5/12; A61B 5/4064; A61B 5/486; A61B 5/6802; A61B 5/6814; A61B 5/30; G16H 50/20; G06F 21/32; G06F 3/015; G06V 40/19
See application file for complete search history.

(56) References Cited

U.S. PATENT DOCUMENTS

| | | |
|---|---|---|
| 2009/0063866 A1 | 3/2009 | Navratil et al. |
| 2016/0103487 A1 | 4/2016 | Crawford et al. |
| 2018/0012009 A1 | 1/2018 | Furman et al. |

OTHER PUBLICATIONS

Schalk, et al, "Brain Sensors and Signals," A Practical Guide to Brain-Computer Interfacing with BC12000, http://www.springer.com/978-1-84996-091-5, 2010, pp. 9-35.
Cecotti, et al, "Convolutional Neural Networks for P300 Detection with Application to Brain-Computer Interfaces," IEEE Transactions on Pattern Analysis and Machine Intelligence, vol. 33, No. Mar. 2011, pp. 433-445.
Malmivuo, et al, "Principles and Applications of Bioelectric and Biomagnetic Fields," www.biolabor.hu, Jan. 1995, pp. 364-374.

(Continued)

*Primary Examiner* — Deborah L Malamud
(74) *Attorney, Agent, or Firm* — Berkeley Law & Technology Group, LLP

(57) ABSTRACT

Briefly, example methods, apparatuses, and/or articles of manufacture are disclosed that may be implemented, in whole or in part, using one or more processing devices to facilitate and/or support one or more operations and/or techniques for authenticating an identity of a human subject. In particular, some embodiments are directed to techniques for authentication of an identity of a human subject as being an identity of a particular unique individual based, at least in part, on involuntary responses by the human subject to sensory stimuli.

20 Claims, 6 Drawing Sheets

(56) References Cited

OTHER PUBLICATIONS

Kus, et al, "On the Quantification of SSVEP Frequency Responses in Human EEG in Realistic BCI Conditions," PLOS ONE, vol. 8, Issue 10, e77536, www.plosone.org, Oct. 2013, 9 Pages.

Kha, et al, "Real-Time Brainwave-Controlled Interface Using P300 Component in EEG Signal Processing," The 2016 IEEE RIVF International Conference on Computing & Communication Technologies, Research, Innovation, and Vision of the Future, IEEE, 978-1-5090-4134-3/16, 2016, pp. 235-240.

Notification Concerning Transmittal of International Preliminary Report on Patentability and Written Opinion of the International Searching Authority, App. No. PCT/GB2019/052097, dated Aug. 19, 2021, 9 Pages.

Notification of Transmittal of the International Search Report and the Written Opinion of the International Searching Authority, or the Declaration, App. No. PCT/GB2019/052097, dated Oct. 28, 2019, 1 Page.

International Search Report, App. No. PCT/GB2019/052097, dated Oct. 28, 2019, 4 Pages.

Written Opinion of the International Searching Authority, App. No. PCT/GB2019/052097, dated Oct. 28, 2019, 9 Pages.

AUTHENTICATION SYSTEM, DEVICE AND PROCESS

BACKGROUND

1. Field

The present disclosure relates generally to authentication of a human subject.

2. Information

Modern security processes typically employ authentication techniques to verify or confirm an identity of a human subject (e.g., user) as a precondition for secure access to a computing system. The disadvantages of requiring users to remember multiple passwords (which are often many characters long) are well known. Other techniques to authenticate users as a precondition for secure access to a computing system are typically cumbersome and detract from the user experience.

SUMMARY

Briefly, particular implementations are directed to a method comprising: generating a first signal to apply a first sensory stimulus to a human subject, the first sensory stimulus to evoke a particular involuntary response by a particular unique individual; generating a second signal to apply a second sensory stimulus to the human subject, the second sensory stimulus being temporally correlated with the first sensory stimulus; inferring that a third signal indicates the particular involuntary response to the first sensory stimulus by the particular unique individual; and authenticating an identity of the human subject as being an identity of the particular unique individual based, at least in part, on a detected temporal correlation of the third signal and a fourth signal indicating an involuntary response to the second sensory stimulus.

Another particular implementation is directed to an apparatus comprising: one or more processors to generate a first signal to apply a first sensory stimulus to a human subject, the first sensory stimulus to evoke a particular involuntary response by a particular unique individual, and to generate a second signal to apply a second sensory stimulus to the human subject, the second sensory stimulus being temporally correlated with the first sensory stimulus; one or more first sensors to generate a third signal responsive to a first involuntary response by the human subject to application of the first sensory stimulus; and one or more second sensors to generate a fourth signal responsive to a second involuntary response by the human subject to application of the second sensory stimulus, wherein the one or more processors are further to: infer that the third signal indicates the particular involuntary response to the first sensory stimulus by the particular unique individual; and authenticate an identity of the human subject as being an identity of the particular unique individual based, at least in part, on a detected temporal correlation of the third signal and a fourth signal indicating an involuntary response to the second sensory stimulus.

Another particular implementation is directed to an article comprising: a non-transitory storage medium comprising device-readable instructions stored thereon that are executable by a processor to: generate a first signal to apply a first sensory stimulus to a human subject, the first sensory stimulus to evoke a particular involuntary response by a particular unique individual; generate a second signal to apply a second sensory stimulus to the human subject, the second sensory stimulus being temporally correlated with the first sensory stimulus; infer that a third signal indicates the particular involuntary response to the first sensory stimulus by the particular unique individual; and authenticate an identity of the human subject as being an identity of the particular unique individual based, at least in part, on a detected temporal correlation of the third signal and a fourth signal indicating an involuntary response to the second sensory stimulus.

It should be understood that the aforementioned implementations are merely example implementations, and that claimed subject matter is not necessarily limited to any particular aspect of these example implementations.

BRIEF DESCRIPTION OF THE DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

Figure 1:
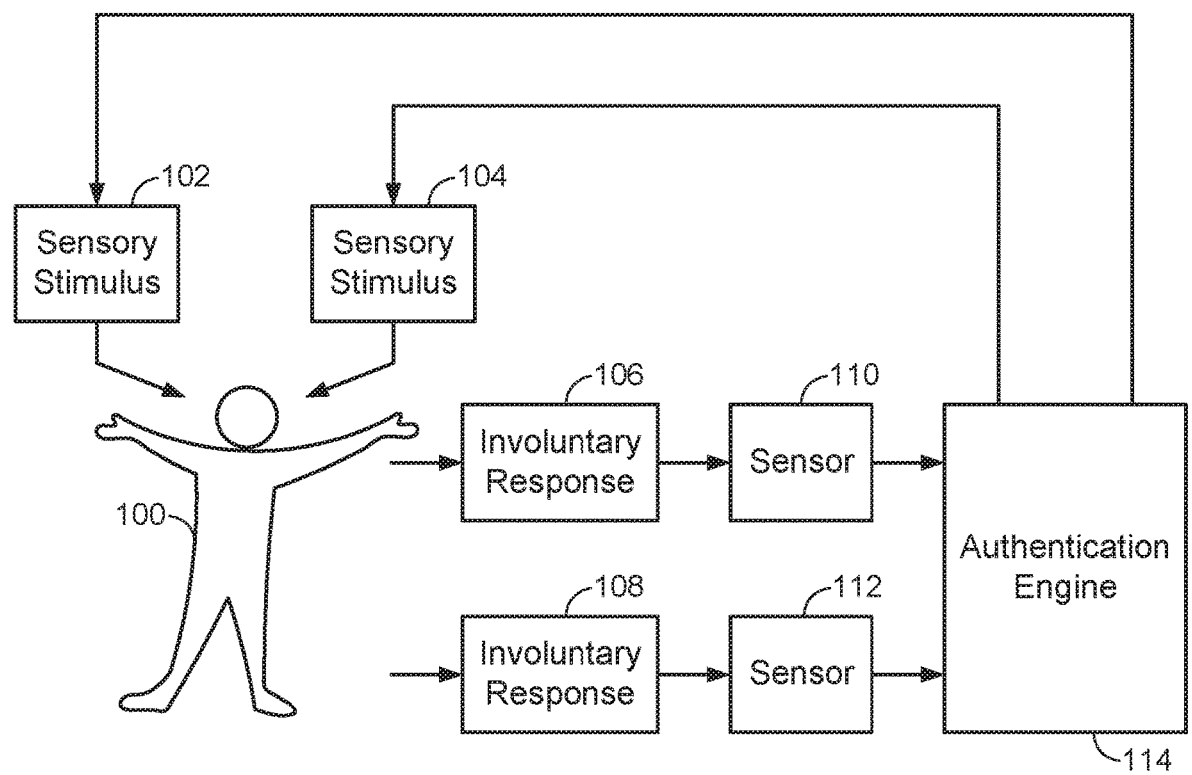
FIG. 1 is a schematic diagram of a system to authenticate a human subject according to embodiments.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter. References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim. It should also be noted that directions and/or references, for example, such as up, down, top, bottom, and so on, may be used to facilitate discussion of drawings and are not intended to restrict application of claimed subject matter. Therefore, the following detailed description is not to be taken to limit claimed subject matter and/or equivalents.

DETAILED DESCRIPTION

References throughout this specification to one implementation, an implementation, one embodiment, an embodiment, and/or the like means that a particular feature, structure, characteristic, and/or the like described in relation to a particular implementation and/or embodiment is included in at least one implementation and/or embodiment of claimed subject matter. Thus, appearances of such phrases, for example, in various places throughout this specification are not necessarily intended to refer to the same implementation and/or embodiment or to any one particular implementation and/or embodiment. Furthermore, it is to be understood that particular features, structures, characteristics, and/or the like described are capable of being combined in various ways in one or more implementations and/or embodiments and, therefore, are within intended claim scope. In general, of course, as has always been the case for the specification of a patent application, these and other issues have a potential to vary in a particular context of usage. In other words, throughout the disclosure, particular context of description and/or usage provides helpful guidance regarding reasonable inferences to be drawn; however, likewise, "in this context" in general without further qualification refers at least to the context of the present patent application.

As more advanced forms of interaction between humans and computers emerge, signals obtained from sensors generated in response to involuntary actions of a human subject (e.g., user) may enable certain enhanced computing services. Sensor signals may exhibit a unique "signature" by being indicative of or responsive to certain internal bodily processes of a human (e.g., involuntary processes). According to an embodiment, a process to authenticate an identity of a human subject may comprise applying one or more sensory stimuli to the human subject and evaluating one or more corresponding involuntary responses by the human subject (e.g., as monitored from sensor signals).

One particular involuntary response by a human subject to sensory stimuli may include brain signals. Electroencephalography (EEG) is a non-invasive technique of detecting, processing and/or recording brain signals including brain signals generated in response to sensory stimuli. Human brain signals may be generated by electrical activity in the brain as neurons exchange information. If a sufficient number of neurons fire simultaneously, electrical patterns associated with a specific region of the brain may be sensed by electrodes placed on or close to the scalp and associated circuitry in proximity to the electrodes. While the spatial resolution of EEG signals may be relatively coarse, EEG signals may be temporally resolved to a sufficient degree after suitable signal amplification and filtering for use in determining command and control signals for a human-computer interface.

FIG. 1 is a schematic diagram of a system to authenticate an identity of a human subject 100 based, at least in part, on involuntary responses 106 and 108 to sensory stimuli 102 and 104 according to embodiments. In a particular implementation, authentication engine 114 may comprise one or more computing devices capable of executing device-readable instructions stored in a non-transitory medium to generate signals initiating sensory stimuli 102 and 104, and process signals from sensors 110 and 112 indicative of involuntary responses (e.g., involuntary responses 106 and 108) from human subject 100 to sensory stimuli 102 and 104.

According to an embodiment, sensors 110 and 112 may generate voltage and/or current signals in response to or indicative of involuntary responses 106 and 108. These voltage and/or current signals may be amplified, filtered, sampled, correlated and otherwise processed to provide a digital signal to be further processed by authentication engine 114 (e.g., by execution of device-readable instructions on a processor). In a particular implementation, sensors 110 and/or 112 may be integrated as part of a brain computer interface (BCI) to detect and measure involuntary responses 106 and 108 as brain signals. Alternatively, sensors 110 and/or 112 may comprise wearable electrodes coupled to (e.g., located by) muscles in the heart or around the lungs, or other portions of the body of human subject 100.

In another alternative implementation, sensors 110 and/or 112 may comprise sensors capable of detecting eye blinking (e.g., for monitoring a frequency of eye blinking), sensors capable of measuring changes in body temperature, changes in electrical impedance or perspiration, just to provide a few additional examples of involuntary responses detectable by sensors. It should be understood, however, that these are merely examples of sensors that are capable of responding to an involuntary response by a human subject (e.g., by generating a voltage and/or current signal), and that claimed subject matter is not limited in this respect.

Sensory stimulus 102 may be associated with an identity of human subject 100, and evoke a corresponding detectable or measurable involuntary response in human subject 100. In other words, sensory stimulus 102 may be selected to evoke a particular involuntary response in a particular unique individual that would not be evoked in another, different human subject. In an implementation, sensory stimulus 102 may be generated from a particular electronic file stored in a library that is selected from or uniquely associated the particular unique individual. In one particular application, a bank or other like financial organization may maintain a library of electronic documents including electric documents associated with identities of clients. For example, a particular electronic document maintained in the library may be used to generate one or more sensory stimuli to evoke a particular involuntary response in a particular unique client associated with the particular electronic document in the library, but not evoke such a particular involuntary response in a human subject other than the particular unique client. In other words, a sensory stimulus generated based on the electronic document, if applied to the particular unique client, may evoke a particular involuntary response in the particular unique client and may not similarly evoke the particular involuntary response if applied to a human subject other than the particular unique client. Other types of organizations and systems may similarly maintain a library of electronic files associated with particular unique individuals for use in authenticating identities of human subjects as being the identities of the particular unique individuals, and claimed subject matter is not limited in this respect. In other implementations, specific computing devices or platforms, such as gaming/virtual reality platforms or electronic equipment where fingerprint scan may be cumbersome or impractical (e.g., in a laboratory, factory or office), may similarly maintain a library of electronic files associated with particular unique individuals for use in authenticating identities of human subjects as being the identities of the particular unique individuals (e.g., as a precondition for access).

Sensory stimulus 102 may comprise, for example, one or more visual images, audible sounds, a haptic stimulus (e.g., application of light pressure or vibrations to various locations of a scalp of human subject 100), just to provide a few examples of sensory stimuli that may evoke a corresponding detectable or measurable involuntary response in a human subject.

In one implementation, sensory stimulus 102 may be provided in a series or stream of sensory stimuli wherein sensory stimulus 102 (e.g., evoking a particular involuntary response in a particular unique individual may not be evoked generally in another human subjects) is temporally interleaved with sensory stimuli that may evoke an involuntary response generally in human subjects. Here, an involuntary response 106 may be detected to be temporally correlated with application of sensory stimulus 102 to human subject 100. For example, if sensory stimulus 102 is selected to evoke a corresponding involuntary response in a particular unique individual (e.g., and not just any individual human being), involuntary response 106 occurring at a particular time relative to a time of application of stimulus 102 may indicate that human subject 100 is indeed the particular unique individual. In an example implementation, application of sensory stimulus 102 may evoke a P300 brain signal in human subject 100. Also, sensory stimulus 102 may be temporally interleaved with other sensory stimuli not expected to evoke a P300 brain signal, enabling detection of involuntary response 106 according to the so-called "odd ball" paradigm.

According to an embodiment, sensory stimulus 104 may comprise a stimulus that evokes a predetermined involuntary response 108 that is temporally correlated with sensory stimulus 102 and involuntary response 106 (evoked by application of sensory stimulus 102). In an implementation, involuntary response 108 may occur independently of application of sensory stimulus 102, and therefore may occur in the presence or absence of involuntary response 106. Also, involuntary response 108 may occur at an expected time lag preceding or following application of sensory stimulus 104, and involuntary response 106 may be expected to occur at a set or predetermined time prior to or following detection of involuntary response 108. Furthermore, application of sensory stimulus 104 may evoke a detectable or distinguishable response generally in multiple different human subjects, not limited to a particular unique individual. In other words, sensory stimulus 104 applied to multiple different human subjects may evoke a similar or like detectable involuntary response 108 in the multiple different subjects at an expect time lag preceding or following application of sensory stimulus 104.

According to an embodiment, sensory stimulus 104 as applied to human subject 100 may be temporally correlated with sensory stimulus 102. For example, sensory stimulus 104 may be applied at a particular instance relative to application of sensor stimulus 102, such as at a set (e.g., predetermined) time preceding or following application of sensory stimulus 102. In a process to authenticate an identity of a particular unique individual, involuntary response 108 (which may be temporally correlated with involuntary response 106) may be used to confirm that a response detected as involuntary response 106 in fact occurs in response to a sensory stimulus 102 (that is to evoke involuntary response 106 in the particular unique individual). In an embodiment, a candidate detection of an involuntary response 106 from a particular unique individual may be confirmed if a corresponding detection of an involuntary response 108 temporally correlates with the candidate detection of the involuntary response 106. This may, for example, reduce or eliminate incidences of false positive authentication of an identity of a human subject as being that of the particular unique individual of interest.

According to an embodiment, if an involuntary response 106 (e.g., evoked in a particular unique individual) is expected, an expected time lag or difference between a time of detection ($t_1$) of an involuntary response 106 and a time of detection ($t_2$) of a temporally correlated involuntary response 108 may be expressed as $\Delta$. Here, if an involuntary response 106 is expected to lead a temporally correlated involuntary response 108 by a duration $\Delta$, detection of an event at time $t_e$ may be confirmed as a detection of an involuntary response 106 in response to a condition at expression (1) as follows:

$$\Delta - \epsilon < t_2 - t_e < \Delta + \epsilon, \qquad (1)$$

Where $\epsilon$ is an error term.

If, on the other hand, an involuntary response 106 is expected to lag a temporally correlated involuntary response 108 by a duration $\Delta$, detection of an event at time $t_e$ may be confirmed as a detection of an involuntary response 106 in response to a condition at expression (2) as follows:

$$\Delta - \epsilon < t_e - t_2 < \Delta + \epsilon. \qquad (2)$$

According to an embodiment, detection of involuntary responses occurring at times $t_1$ and $t_2$ may be performed responsive to detection of particular sensor characteristics (e.g., detection of particular signal characteristics in signals generated by sensors 110 or 112). For example, a time $t_e$ or $t_2$ may be determined based on detection of particular voltage and/or current signals generated by sensor 110 or 112 (e.g., detection of a voltage peak, etc.). In one particular implementation as discussed below, a time $t_2$ may be determined based, at least in part, on a detected occurrence of a frequency characteristic and/or amplitude variation in a signal generated by sensor 112.

According to an embodiment, a time between initiation of sensory stimulus 102 and occurrence of detection of involuntary response 106 may vary from human being to human being due to individual-specific physiology. Likewise, a time between initiation of sensory stimulus 104 and occurrence of detection of involuntary response 108 may similarly vary from human being to human being due to individual-specific physiology. As such, a value for $\Delta$ discussed above in connection with expressions (1) and (2) may vary from human being to human being due to individual-specific physiology. While sensory stimulus 102 may be selected/determined to evoke involuntary response 106 in a particular unique individual, in application of expressions (1) or (2), a particular value for $\Delta$ may be selected/determined based, at least in part, on physiology specific to the particular unique individual. For example, in applying expression (1) or (2) a value of $\Delta$ for a particular unique individual may be determined based, at least in part, on prior observations of involuntary responses by the particular unique individual to sensory stimuli.

Figure 2A:
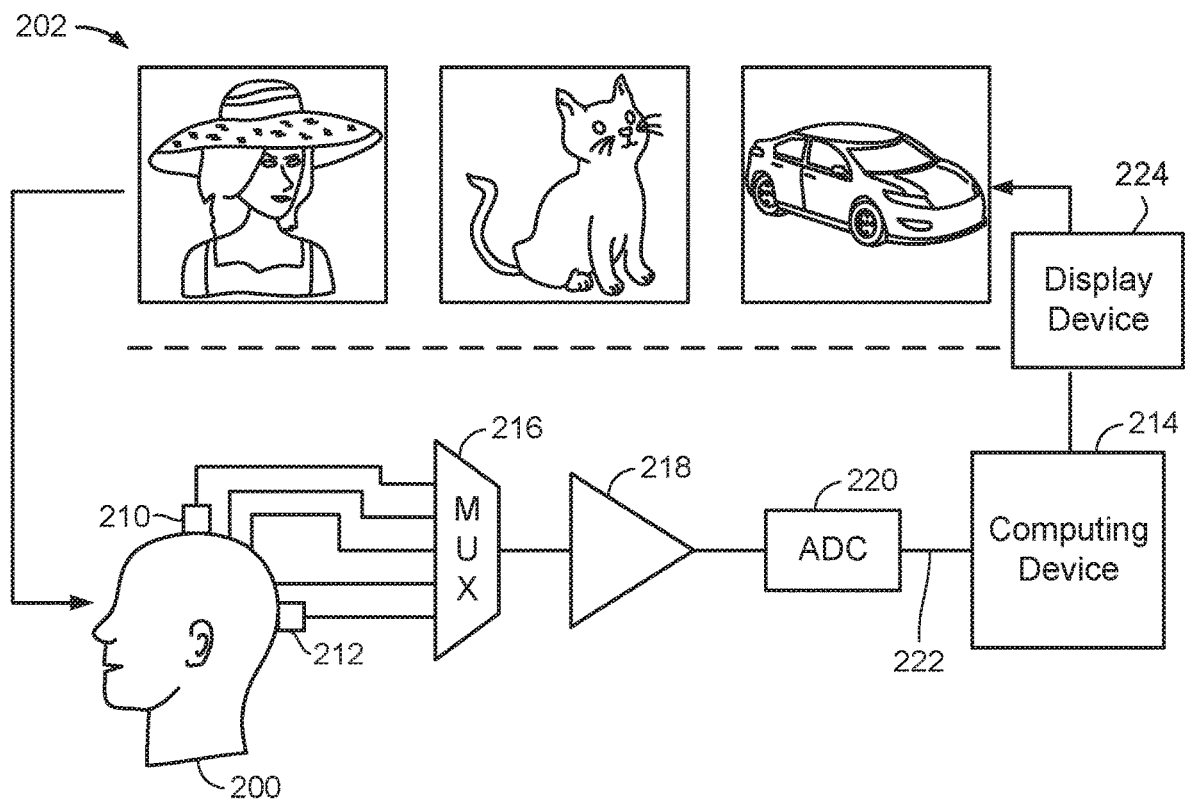
FIG. 2A is a schematic diagram of a system to authenticate a human subject according to particular embodiments.

FIG. 2A is a schematic diagram of a system to authenticate a human subject according to one or more aspects or implementations of the system shown in FIG. 1. A sensory stimulus applied to human subject 200 may comprise presentation to human subject 200 of a series of visual images 202 in which one or more images are of particular significance to a particular unique individual (e.g., a particular individual who may or may not be the same as human subject 200). Presentation of the one or more images of particular significance to the particular unique individual may further be temporally interleaved with presentation of random images that are of no particular significance to the particular unique individual. The image of particular significance to the particular unique individual may comprise, for example, an image of something of personal significance to the particular unique individual such as a portrait of a family member, childhood scene or other image that potentially evokes an "attention grabbing" response in the particular unique individual (but not generally in individuals other than the particular unique individual). In an embodiment of an authentication process, if presentation to human subject 200 of the one or more images of particular significance evokes such an attention grabbing response (e.g., involuntary response) in human subject 200, it may be inferred that an identity of human subject 200 is the identity of the particular unique individual.

According to an embodiment, a brain computer interface (BCI) may detect, process and/or characterize brain signals generated by human subject 200 in response to sensory stimuli. For example, sensors 210 and 212 may be adapted to be in contact with a scalp of human subject 200 to, among other things, generate voltage and/or current signals characterizing signals occurring in a brain of human subject 200 in response to sensory stimuli. Sensors 210 and 212 may comprise, for example, any one of several electrodes suitable for non-invasive placement on the scalp of human subject 200 to support electroencephalography (EEG) brain signal processing. In a particular implementation, sensors 210 and 212 may be attached to specific positions on a headset (not shown) to precisely position sensors 210 and 212 on specific locations of the scalp of human subject 200. For example, sensors 210 and 212 may be integrated with a virtual reality (VR) headset including one or more audio speakers, a microphone and one or more display devices (e.g. implemented as display device 224) for displaying images. In alternative implementations, sensors 210 and 212 may comprise electrodes that are placed on the surface of a brain of human subject 200 to support electrocorticography (ECoG), or may comprise electrodes placed invasively within the brain of human subject 200 to support single-neuron recordings. It should be understood that these are merely examples of sensors that may be integrated as part of a BCI, and claimed subject matter is not limited in this respect.

A BCI to process voltage and/or current signals generated by sensors 210 and 212 may further include multiplexer (MUX) 216, buffer/amplifier 218 and analog-to-digital converter (ADC) 220. In an implementation, sensors 210 and 212, MUX 216, buffer/amplifier 218 and ADC 220 may be integrated in a headset adapted to be fitted to the scalp of human subject 200 for proper placement of sensors 210 and 212 in contact with particular locations of the scalp of human subject 200. ADC 220 may be coupled to computing device 214 by a communication link 222 having suitable data throughput and low latency such as, for example, a wired communication link (e.g., Universal Serial Bus) or wireless communication link (e.g., Bluetooth® or version of IEEE std. 802.11), just to provide a few examples. In an embodiment, messages may be transmitted in signal packets or signal frames between ADC 220 and computing device 214, and may be encrypted to enhance security to avoid hacking of an authentication process, for example.

According to an embodiment, MUX 216 may comprise specialized processing hardware to assist in combining signals generated by multiple sensors including sensors 210 and 212. In one particular example, MUX 216 may comprise a machine-learning processor to assist in fusing, filtering or otherwise processing current and/or voltage signals generated by sensors 210 and 212, and classification of detected signal characteristics for use in additional processing. In one particular implementation, MUX 216 may be configured to implement one or more techniques for detection and classification of P300 brain signals based on current and/or voltage signals generated by sensors 210 and 212 such as described in H. Cecotti and A. Graser "Convolutional Neural Networks for P300 Detection with Application to Brian-Computer Interfaces," IEEE Transactions on Pattern Analysis and Machine Intelligence, Vol. 33, No. 3, March 2011, or described in Ha Hoang Kha and Vo Anh Kha, "Real-Time Brainwave-Controlled Interface Using P300 Component in EEG Signal Processing," The 2016 IEEE RIVF International Conference on Computing & Communication Technologies, Research, Innovation, and Vision for the Future. In another particular implementation, MUX 216 may be configured to implement one or more techniques for detection and classification of steady-state visual evoked potential (SSVEP) signals based on current and/or voltage signals generated by sensors 210 and 212 such as described in Rafal Kus, Anna Duszyk, Piotr Milonowski, Maciej Labecki, Maria Bierzynska, Zofia Radzikowka, Magdalena Michalska, Jaroslaw Zygierewicz, Piotr Suffcznski and Piotr Jerzy Durka, "On the Quantification of SSVEP Frequency Responses in Human EEG in Realistic BCI Conditions," PLOS ONE, Volume 8, Issue 10, October 2013. MUX 216 may also perform other signal processing and condition operations including, for example and without limitation, adjustments of bias and/or dynamic range of signals. It should be understood, however, that these are merely examples of how MUX 216 may be configured to process current and/or voltage signals generated by sensors 210 and 212, and that claimed subject matter is not limited in this respect.

According to an embodiment, computing device 214 may control presentation of visual images 202 for viewing by human subject 200 through display device 224 such as, for example, an LED display device and/or a projector. As discussed herein, display device 224 may be positioned over eyes and integrated as part of a VR headset including speakers, microphone and sensors 210 and 212 positioned for placement at specific locations of the scalp of human subject 200. In one implementation, computing device 214 may control timing of a sequence of presentation of visual images 202 through display device 224 according to a time reference such as a time reference to a clock signal. In an embodiment, a BCI formed by sensors 210 and 212, MUX 216, buffer/amplifier 218 and ADC 220 may apply "time stamps" to observations of brain signals detected at sensors 210 and 212. These time stamps may be referenced to the time reference that is maintained by computing device 214 and is used in controlling timing of the sequence of presentation of visual images 202.

An image of significance to a particular unique individual in or among visual images 202 may evoke a so-called "P300" brain signal in human subject 200 (e.g., if human subject 200 happens to in fact be the particular unique individual), which may comprise a detectable brain signal that is produced at a particular delay (e.g., at a delay of about 300 ms depending on a particular physiology of human subject 200) after the application of interesting (e.g., attention-grabbing) but unexpected sensory stimulus such as a visual image. Detection of such a P300 brain signal may rely on the aforementioned "odd-ball" paradigm in which presentations of sequences of repetitive stimuli are infrequently interrupted by a deviant stimulus. In this case, a deviant stimulus may comprise a visual image of significance to the particular unique individual among other images of no particular significance to the particular unique individual. A reaction of a human subject to such an "oddball" stimulus may be recorded. In a particular implementation, sensors, such as sensors 210 and 212, may be attached to the scalp of human subject 200 to detect a P300 brain signal generated by human subject 200 in response to the oddball stimulus.

Figure 2B:
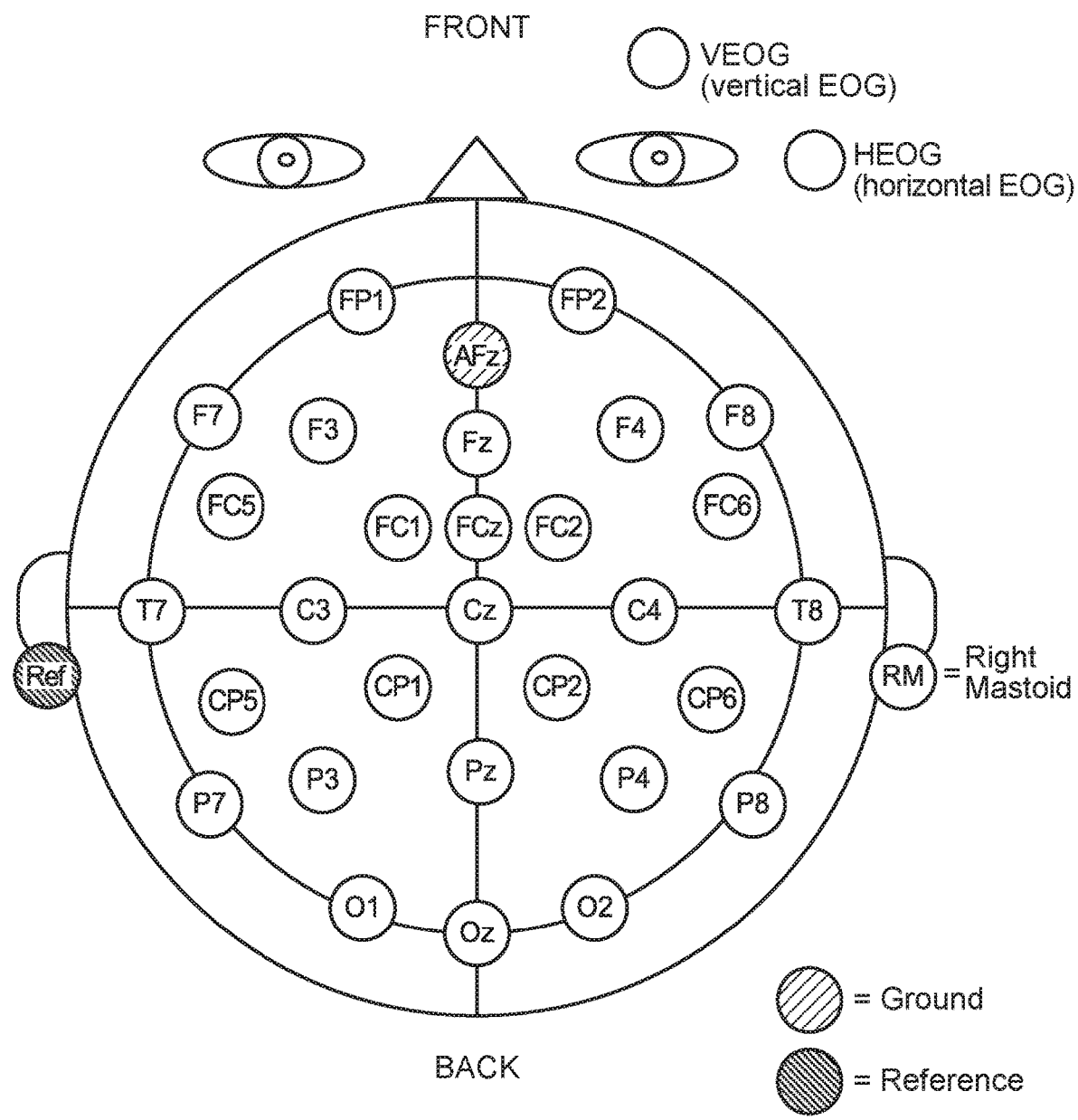
FIG. 2B is a schematic diagram illustrating possible locations on a human scalp for positioning sensors for brain signal detection according to particular embodiments.

Exact placement of sensors on locations of a human scalp for effective detection of brain signals may vary between human subjects. FIG. 2B is a schematic diagram illustrating possible placement of sensors, such as sensors 210 and 212, on locations of the scalp of human subject 200 (e.g., from sensors 210 and 212 integrated in a VR headset). Those skilled in the art may recognize that sensors may be positioned on locations of the scalp of a human subject according to a scheme such as the international 10-20 system, describing suitable locations on the scalp for a range of purposes. Locations on the scalp for placement of sensors may be selected based, at least in part, on proximity to certain brain regions of interest. In the particular implementation of FIG. 2B, for example, positions for favorable P300 brain signal detection in one embodiment may include F3, F4, FC5, FC6, P7 and P8.

An image of significance (to a particular unique individual) in visual images 202 may be temporally correlated with a different image or visual stimulus in visual images 202 such that the different image evokes a detectable brain signal that is temporally correlated with a P300 signal generated by human subject 200 in response to the image of significance. For example, such a different image or other visual stimulus in images 202 may comprise an image or visual stimulus capable of evoking a detectable brain signal as a so-called steady-state visual evoked potential (SSVEP) brain signal in human subject 200 (e.g., which are detectable by sensors 210 and/or 212). In an embodiment, SSVEP brain signals may comprise responses to visual stimulation at specific frequencies. For example, a human retina excited by a visual stimulus having a temporal frequency ranging from 3.5 Hz to 75 Hz may initiate electrical activity in a human brain at the same (or multiples of) frequency of the visual stimulus.

In this particular implementation, in addition to applying a first sensory stimulus as a visual image of significance to a particular unique individual, series of visual images 202 may apply a second sensory stimulus comprising one or more visual images and/or visual stimuli that are temporally correlated with the visual image of significance to the particular unique individual. For example, the second sensory stimulus may comprise presentation of a visual image in series of visual images 202 that precedes or follows the visual image of significance to the particular unique individual by a predetermined and/or set time lag. Additionally, the visual image and/or visual stimuli providing the second sensory stimulus may comprise one or more frequency components having a predetermined and/or known frequency to evoke in human subject 200 a corresponding detectable SSVEP brain signal. This SSVEP brain signal may be temporally correlated with a P300 signal evoked in human subject 200 in response to the visual image of significance to a particular unique individual in series of images 202. For example, detection of such an SSVEP brain signal may lead or lag detection of the P300 signal by a known or predetermined duration. In an embodiment, an inference that an identity of human subject 200 is the identity of the particular unique individual may be based on detection of a signal classified as a P300 brain signal (e.g., indicating an involuntary response by the particular unique individual) may be confirmed based, at least in part, on detection of an SSVEP brain signal at a particular time relative to a time of detection of the signal classified as a P300 brain signal.

According to an embodiment, a signal detected as an SSVEP brain signal may be temporally correlated with a signal initially classified as a P300 brain signal, at least in part, on features in the signal detected as an SSVEP brain signal. One such feature in the signal detect as an SSVEP brain signal to be temporally correlated with a signal initially classified as a P300 brain signal may comprise a frequency characteristic such as a temporal frequency that is an integer multiple of a temporal frequency in a corresponding visual stimulus. Another such feature in the signal detected as an SSVEP signal to be temporally correlated with a signal initially classified as a P300 brain signal may comprise a variation in a signal magnitude.

Figure 3:
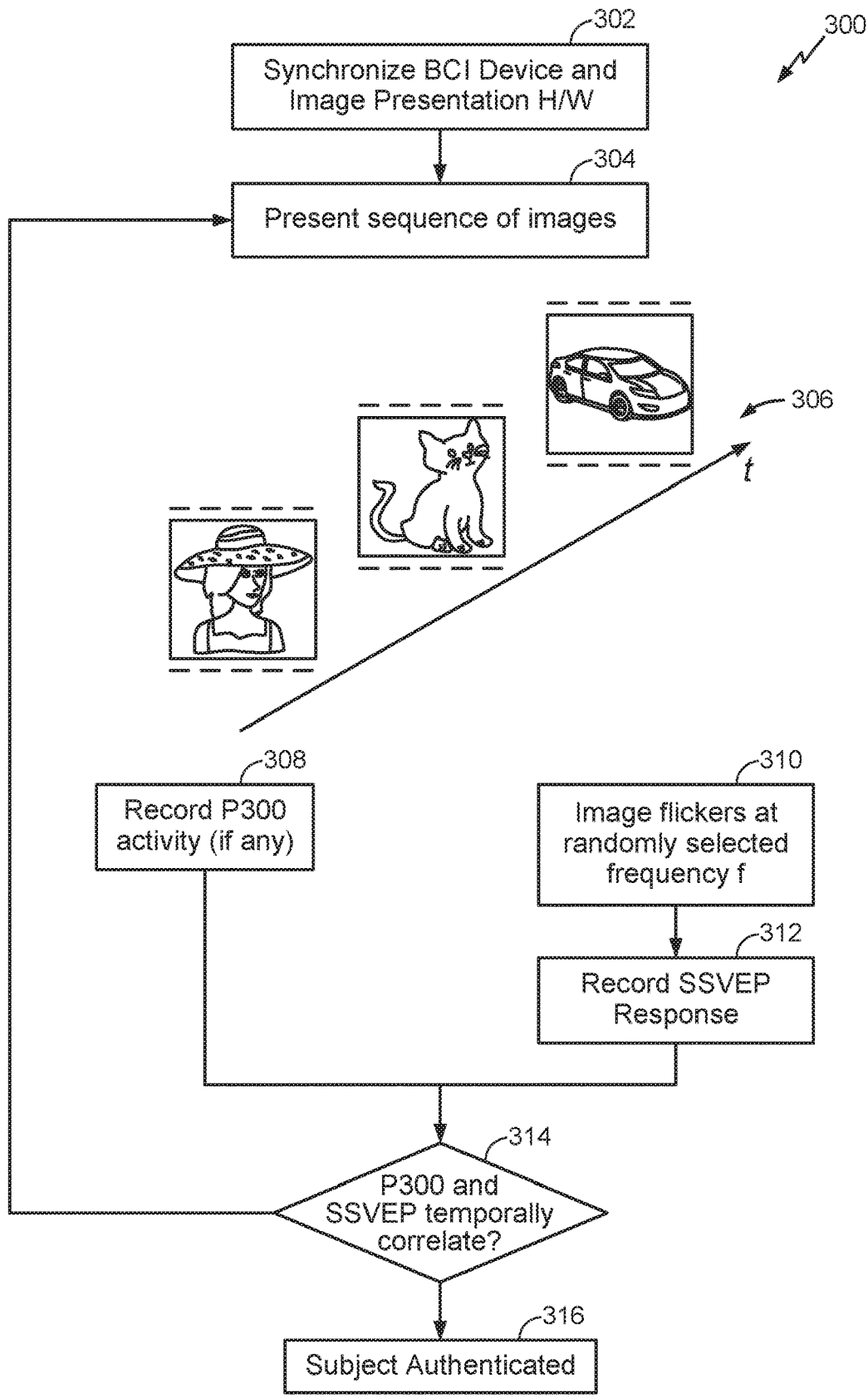
FIG. 3 is a flow diagram of a process to authenticate a human subject according to an embodiment.

In an embodiment, an inference that an identity of human subject 200 is the identity of the particular unique individual based on detection of a signal classified as a P300 brain signal (e.g., indicating an involuntary response by the particular unique individual) may be confirmed based, at least in part, on detection of an SSVEP brain signal at a particular time relative to a time of detection of the signal classified as a P300 brain signal as illustrated in process 300 according to FIG. 3. For example, if such a signal classified as a P300 brain signal is detected at a time $t_e$, an SSVEP brain signal is detected at a time $t_2$ and detection of the P300 brain signal is expected to lead detection of the SSVEP brain signal by a duration $\Delta$, an identity of human subject 200 may be authenticated as being the identity of a particular unique individual if a condition set forth in expression (1) is satisfied. Alternatively, if such a signal classified as a P300 brain signal is detected at a time $t_e$, an SSVEP brain signal is detected at a time $t_2$ and detection of the P300 brain signal is expected to lag detection of the SSVEP brain signal by a duration $\Delta$, an identity of human subject 200 may be authenticated as the identity of a particular unique individual if a condition set forth in expression (2) is satisfied.

As pointed out above, values for $\Delta$ as applied in expressions (1) and (2) may vary based, at least in part, on a physiology of the particular unique individual. For example, a difference between presentation of a visual image of significance and detection of a responsive P300 brain signal may vary based on human physiology. For example, physiology of a particular human may uniquely affect a latency in processing a visual image commencing with exposure of a retina of the particular human, followed by cognitive recognition of the image captured at the retina and followed by generation of a P300 brain signal. Likewise, a difference between presentation of a visual stimulation at a particular temporal frequency and detection of a responsive SSVEP brain signal may vary based on human physiology. As such, a value for $\Delta$ may be determined and/or selected based, at least in part, expected response times by the particular unique individual to presentation of the visual image of significance and visual stimulation at the particular temporal frequency.

It may be observed that in particular implementations, particular characteristics of an SSVEP brain signal generated by a human (e.g., responsive to a visual stimulus at a particular temporal frequency) may be affected by a physiology of the human. For example, a particular frequency characteristic in an SSVEP brain signal (e.g., a frequency shift at an integer multiple of a temporal frequency of a visual stimulus) may vary from individual to individual in a predictable manner. Additionally, a magnitude of a voltage level of an SSVEP brain signal may vary from individual to individual. Thus, in an embodiment, an SSVEP brain signal generated by a particular unique individual may have features that are unique for that particular unique individual. Accordingly, in addition to evaluating a temporal correlation of a detected P300 brain signal and a detected SSVEP brain signal, a process may further compare features of the detected SSVEP brain signal with features expected in an SSVEP brain signal (e.g., magnitude of frequency shift or voltage level) for that particular unique individual.

In a particular implementation, actions illustrated in FIG. 3 may be performed and/or executed at least in part by elements or features of the system shown in FIG. 2A (e.g., computing device 214, MUX 216, ADC 220, display devices, etc.). Block 302 may comprise synchronization of a brain computer interface (BCI) with signals controlling timing of presentation of a sequence of visual images such as visual images 202 through image presentation hardware such as display device 224. As pointed out above in the particular implementation of FIG. 2A, computing device 214 may comprise circuitry to maintain a clock state for controlling timing of presentation of visual images 202 in a particular sequence. MUX 216 may, in a particular implementation, comprise circuitry to maintain a clock state for use in determining time stamps to be applied to observations of brain signals detected based on voltage and/or current signals generated by sensors 210 and 212. Here, using in-band or out-of-band signalling, computing device 214 and MUX 216 may exchange messages to synchronize clock states maintained at computing device 214 and MUX 216 to a common time reference. This may enable time stamps applied to observations of brain signals detected based, at least in part, on voltage and/or current signals generated by sensors 210 and 212 to be temporally associated with images presented to human subject 200 according to the common time reference.

According to an embodiment, block 304 may comprise presentation of visual images 306 to a human subject by applying signals to one or more display devices. As pointed out above, block 304 may present to a human subject at least some visual images 306 at known instances according to a time reference. For example, block 304 may present a visual image of significance (e.g., evoking a P300 brain signal) in visual images 306 at a particular known time (e.g., according to the time reference). While visual images 306 are presented to a human subject via one or more display devices, detectable brain signals generated by the human subject may be monitored based, at least in part, on voltage and/or current signals generated by sensors (e.g., sensors 210 and/or 212) positioned on particular locations of the scalp of human subject 200.

In one particular implementation, while visual images 306 are being presented to a human subject, one or more sensors may be positioned to be in contact with one or more locations of the human subject's scalp to detect particular brain signals of interest (e.g., P300 brain signals and/or SSVEP brain signals described above). Block 308 may continually monitor voltage and/or current signals from one or more sensors to detect generation of a P300 brain signal by the human subject. As discussed above, detection of such a P300 brain signal may occur responsive to an involuntary response by the human subject to a particular visual image among visual images 306 that is of particular relevance or significance to a particular unique individual (e.g., a portrait of a family member, childhood scene or other image that potentially evokes an "attention grabbing" response in the particular unique individual).

As discussed above, in addition to including a visual image of significance (e.g., evoking generation of a P300 brain signal in a brain of a particular unique individual), visual images 306 may also include another, different visual image and/or visual stimulus expected to precede or follow the visual image significance by a predetermined and/or known time lag. In an embodiment, a visual image of significance in visual images 306 may be presented to a human subject for a suitable duration to enable a reliable detection of a P300 brain signal in the human subject. Following beginning of a presentation of a visual image of significance in visual images 306, block 310 may be caused to "flicker" presentation of the visual image of significance at a particular frequency. For example, a visual image of significance in visual images 306 may be presented for 0.5 seconds followed by a flickering of the visual image of significance at a particular frequency (e.g., a particular frequency "f") as indicated by block 310. Block 312 may comprise detecting an involuntary response from the human subject to the flickering of the visual image of significance at block 310. For example, block 312 may detect an SSVEP brain signal having a frequency component that is at the particular frequency at which this visual image is flickered at block 310 or some multiple thereof.

Since flickering of the visual image of particular significance to a particular unique individual commences at block 310 a predetermined and/or known time lag following commencement of presentation of the visual image of significance (e.g., 0.5 seconds), detection of a P300 brain signal at block 308 (occurring at about 300 msec following commencement of presentation of the visual image of significance) and detection of a SSVEP brain signal at block 312 may occur roughly simultaneously or at a predetermined and/or known separation in time. As pointed out above, a predetermined and/or known separation of time between detections of a P300 brain signal at block 308 and an SSVEP brain signal at block 312 may vary depending on factors such as a particular physiology of a human subject receiving presentation of the visual stimulus. Accordingly, a genuine detection of a P300 signal at block 308 in response to presentation of visual image of particular significance to a particular unique individual should expected to be accompanied by detection of a corresponding SSVEP brain signal at block 312 at a predetermined and/or known delay and signal magnitude.

Diamond 314 may perform an association of activity recorded at blocks 308 and 310 to confirm that a signal classified as a P300 brain signal is indeed a P300 brain signal evoked as an involuntary response to a sensory stimulus. Referring to expression (1) and (2) above, a time of detection at block 308 of a signal classified as a P300 brain signal may have a value $t_e$, a time of detection at block 310 of an SSVEP signal at block 312 may have a value of $t_2$ and an expected difference between a time of detection ($t_1$) of an actual P300 brain signal at block 308 and detection of an SSVEP signal at block 310 may have a value $\Delta$. If detection of the P300 brain signal at block 308 is expected to lead detection of the SSVEP signal at block 310 by $\Delta$, diamond 314 may then determine whether the signal classified as a P300 brain signal is indeed a P300 brain signal (evoked in the brain of a particular unique individual) if the condition of expression (1) is satisfied. Likewise, If detection of the P300 brain signal at block 308 is expected to lag detection of the SSVEP signal at block 310 by $\Delta$, diamond 314 may then determine whether the signal classified as a P300 brain signal is indeed a P300 brain signal (evoked in the brain of a particular unique individual) if the condition of expression (2) is satisfied. In either case, block 316 may authenticate an identity of a human subject as an identity of a particular unique individual.

As pointed out above, diamond 314 may temporally correlate a signal recorded as an SSVEP brain signal at block 312 with a signal recorded as a P300 brain signal at block 308 based, at least in part, on features in the signal recorded as the SSVEP brain signal at block 312. For example, diamond 314 may comprise temporally correlating an occurrence of a frequency characteristic in the signal recorded as an SSVEP brain signal at block 312 (such as a temporal frequency that is an integer multiple of a temporal frequency in a corresponding visual stimulus) and/or occurrence of signal magnitude variation in the signal recorded as the SSVEP brain signal at block 312.

As pointed out above, in addition to a temporal correlation determined at diamond 314, in a particular implementation authentication of a subject at block 316 may be further based on features of the SSVEP signal recorded at block 312. As pointed out above, features of the SSVEP signal recorded at block 312 (e.g., magnitude of frequency shift in SSVEP signal based on particular flicker frequency "f" and magnitude in signal voltage variation) may vary based on particular physiological characteristics of a human subject. Accordingly, to obtain further confidence in an authentication, block 316 may further determine whether features in the SSVEP brain signal recorded at block 312 sufficiently match expected features in an SSVEP brain signal evoked in the particular unique individual in response to flickering an image at block 310.

Figure 4:
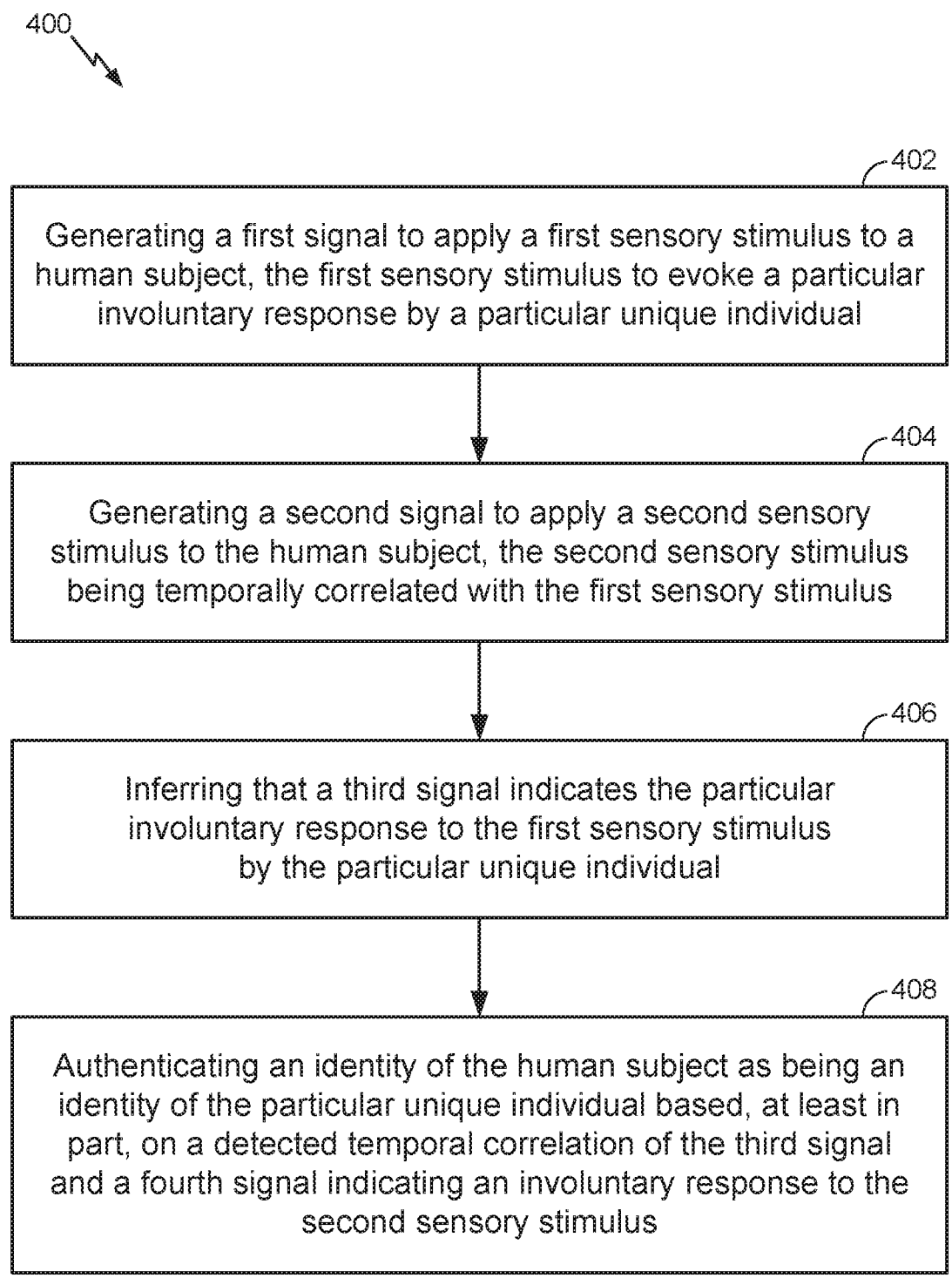
FIG. 4 is a flow diagram of an aspect of a process to authenticate a human subject according to an embodiment.

FIG. 4 is a flow diagram of an aspect of a process 400 to authenticate an identity of a human subject according to an embodiment. Block 402 may comprise generating a first signal to apply a first sensory stimulus to a human subject. For example, block 402 may comprise computing device 214 generating a signal to display device 224 for presentation of a visual image of significance to the human subject to evoke generation of a P300 brain signal in the human subject. As pointed out above, such a visual image of significance may comprise an image of significance to a particular unique individual. For example, the image of significance to the particular unique individual may comprise a portrait of a family member, childhood scene or other image, just to provide a few examples, that potentially evokes an "attention grabbing" response in the particular unique individual. It should be understood, however, that in alternative embodiments the a first sensory stimulus to a human subject applied by block 402 may comprise providing content and/or control signals to specific devices (e.g., speakers, haptic devices, etc.) to apply audible sounds or a haptic stimulus (e.g., application of light pressure or vibrations to various locations of a scalp of a human subject), just to provide a few examples of additional sensory stimuli that may evoke a corresponding detectable or measurable involuntary response in a human subject.

As discussed herein in connection with a particular implementation, the first signal may be generated at block 402 from an electronic document maintained in a library stored on one or more device-readable storage mediums. In an example, a computing device (such as computing device 214) may fetch the electronic document from the device-readable medium, and execute device readable instructions to generate the first signal. In an embodiment, the electronic document may be stored in a library of electronic documents stored on the device-readable medium and may be fetched based, at least in part, on a unique identifier associated with the particular unique individual. For example, the fetched electronic document may be accessed in the library based on an associated identifier such as a first/last name, social security number and/or other personal attributes unique to the particular unique individual. According to an embodiment, the fetched electronic document may comprise media content (e.g., still images, audio, video, etc.) encoded in a particular format (e.g., JPEG, MPEG, MP3, etc.). By execution of device readable instructions, a computing device executing block 402 may decode portions of the fetched electronic document to provide the first signal as control and/or content signals to one or more output devices for applying sensory stimuli to a human subject. For example, block 402 may construct a signal to drive a display device (e.g., display device 224) for presentation of a series of video frames based on media content in the electronic document that has been decoded. As pointed out above, such a series of video frames may present one or more images of particular significance to the particular unique individual (e.g., potentially evoking a P300 brain signal in the particular unique individual). In an example implementation, video frames presented in response to the first signal may be temporally interleaved with other video frames presenting images other than visual images of particular significance to the particular unique individual (e.g., to enable detection of a P300 brain signal according to the odd-ball paradigm).

Block 404 may comprise generating a second signal to apply a second sensory stimulus to the human subject that is temporally correlated with the first sensory stimulus applied based on based on the first signal generated by block 402. For example, block 404 may be executed at least in part by computing device 214 generating a signal to a display device (e.g., display device 224) for presentation of a second visual image at a set duration preceding or following generation of a first visual image. As pointed out above, an involuntary response to a first sensory stimulus applied at block 402 may comprise a P300 brain signal occurring in the brain of the human subject. The second visual image may comprise a visual image having a temporal frequency component evoking a detectable SSVEP brain signal in the human subject. For example, the second visual image may comprise a flickering of the first visual image at a randomly selected frequency and beginning at a known duration following a start of a presentation of the first visual image such as at block 310. In an implementation, a computing device (e.g., computing device 214) may execute instructions fetched from a device-readable medium to affect a flickering of an image at a particular or predetermined temporal frequency.

In a particular implementation in which block 402 constructs the first signal to drive a display device for presentation of one or more visual images from a series of video frames, block 404 may comprise modifying a portion of video frames in the series of video frames. For example, a computing device may construct a media and/or control signal comprising a series of video frames including a first portion of video frames to present one or more visual images of particular significance to the particular unique individual. Block 404 may comprise a modification to a second portion of video frames at a predetermined or known temporal separation from the first portion of video frames. In an implementation, the second portion of video frames may be modified by imparting a flickering in resulting visual images (e.g., at a known frequency) to evoke an SSVEP brain signal in a human subject.

Block 406 may comprise inferring that a collected third signal indicates the particular involuntary response by the human subject to the first sensor stimulus applied at block 402. As pointed out in a particular implementation, a sensor positioned at a particular location of a human subject's scalp may generate voltage and/or current signals indicative of or responsive to involuntary responses (e.g., brain signals) to sensory stimuli. As pointed out above, such sensors may comprise any one of several electrodes suitable for non-invasive placement on the scalp to support electroencephalography (EEG) brain signal processing. It should be understood, however, that third signals may be generated at block 406 by different types of sensors including, for example, sensors capable of detecting and/or measuring other types of involuntary responses as discussed herein. In a particular example, block 406 may infer that the third signal is indicative of or generated in response to an occurrence of a P300 brain signal evoked in response to the first sensory stimulus applied at block 402. For example, block 406 may comprise recording of P300 brain signal activity at block 308.

According to an embodiment, an inference at block 406 that the third signal indicates an involuntary response to the first sensory stimulus by the particular unique individual may be false. For example, block 406 may comprise detection of a signal having one or more attributes of a P300 brain signal at block 308, which may or may not comprise a correct positive detection of a P300 brain signal. Further processing may enable additional confidence that a collected third signal (e.g., appearance of a P300 brain signal based on activity detected at block 308) indeed is a particular involuntary response by a particular unique individual of interest. Block 408 may comprise authenticating an identity of a human subject as being an identity of a particular unique individual based, at least in part, on a detected temporal correlation of the third signal and a fourth signal indicating an involuntary response (e.g., an involuntary response which matches a given individual's expected or predetermined response stored in a repository expected responses) to the second sensory stimulus applied at block 408. In an implementation, block 408 may determine a detected temporal correlation of the third signal and fourth signal as illustrated at diamond 314. For example, the third signal may comprise a P300 brain signal detected by block 308 at a time $t_e$, the fourth signal may comprise an SSVEP brain signal detected by block 312 at time $t_2$ and an expected lag between detection of a P300 brain signal and temporally correlated SSVEP brain signal may be $\Delta$. If detection of the third would be expected to lead detection of the fourth signal, the identity of the human subject may be authenticated if the condition of expression (1) is met. Likewise, if detection of the third would be expected to lag detection of the fourth signal, the identity of the human subject may be authenticated if the condition of expression (2) is met.

In particular implementation, block 408 may further base authentication of an identity of a human subject on features in the fourth signal. As pointed out above, the fourth signal may comprise an SSVEP brain signal with signal characteristics (e.g., magnitude of frequency shift and voltage) that may vary based on a particular physiology of the human subject. Here, block 408 may further base authentication of the identity of the human subject on whether features in the fourth signal sufficiently match features in the fourth signal that would be expected if evoked in the unique particular individual responsive to the second sensory stimulus. For example, if the fourth signal comprises an SSVEP brain signal evoked in the human subject responsive to the second sensory stimulus, block 408 may further base authentication of the identity of the human subject on whether a magnitude in frequency response and/or voltage in the SSVEP brain signal sufficiently match an expected magnitude in frequency response and/or voltage in an SSVEP brain signal to be evoked by the particular unique individual in response to the second sensory stimulus.

As pointed out above, block 402 may retrieve an electronic document fetched from a library of electronic documents stored on a device-readable medium. In addition to containing media content for use in generating the first signal, the electronic document may comprise additional parameters corresponding to the particular unique individual for application by block 408 in authentication of the human subject. For example, the electronic document may comprise a value for $\Delta$ to be applied in expression (1) or (2) in determining whether the third signal (e.g., signal detected as a P300 brain signal) temporally correlates with the fourth signal (e.g., SSVEP brain signal). The value for $\Delta$ may be determined and/or selected based, at least in part, expected response times by the particular unique individual to the first and second sensory stimuli (e.g., based, at least in part, expected response times by the particular unique individual to presentation of the visual image of significance to evoke a P300 brain signal and visual stimulation at the particular temporal frequency to evoke an SSVEP brain signal). In addition to containing media content for use in generating the first signal and/or a value for $\Delta$, the electronic document may comprise additional parameters corresponding to expected features in the fourth signal if evoked in the unique particular individual responsive to the second sensory stimulus. As discussed above, these parameters corresponding to expected features in the fourth signal (e.g., magnitude of frequency shift and/or voltage in an SSVEP signal) may then be compared with actual features in the fourth at block 408 for added confidence in an authentication of the identity of the human subject.

According to an embodiment, values for $\Delta$ stored in an electronic document may be initially determined in a training process in which repeated stimuli are applied to the particular unique individual while brain signals are monitored and measured. Likewise, additional parameters stored in an electronic document corresponding to expected features in a fourth signal (e.g., magnitude of frequency shift and/or voltage in an SSVEP signal) may be determined in a training process in which the second stimulus is repeatedly applied to the particular unique individual while brain signals are monitored and measured.

In the context of the present patent application, the term "connection," the term "component" and/or similar terms are intended to be physical, but are not necessarily always tangible. Whether or not these terms refer to tangible subject matter, thus, may vary in a particular context of usage. As an example, a tangible connection and/or tangible connection path may be made, such as by a tangible, electrical connection, such as an electrically conductive path comprising metal or other conductor, that is able to conduct electrical current between two tangible components. Likewise, a tangible connection path may be at least partially affected and/or controlled, such that, as is typical, a tangible connection path may be open or closed, at times resulting from influence of one or more externally derived signals, such as external currents and/or voltages, such as for an electrical switch. Non-limiting illustrations of an electrical switch include a transistor, a diode, etc. However, a "connection" and/or "component," in a particular context of usage, likewise, although physical, can also be non-tangible, such as a connection between a client and a server over a network, particularly a wireless network, which generally refers to the ability for the client and server to transmit, receive, and/or exchange communications, as discussed in more detail later.

In a particular context of usage, such as a particular context in which tangible components are being discussed, therefore, the terms "coupled" and "connected" are used in a manner so that the terms are not synonymous. Similar terms may also be used in a manner in which a similar intention is exhibited. Thus, "connected" is used to indicate that two or more tangible components and/or the like, for example, are tangibly in direct physical contact. Thus, using the previous example, two tangible components that are electrically connected are physically connected via a tangible electrical connection, as previously discussed. However, "coupled," is used to mean that potentially two or more tangible components are tangibly in direct physical contact. Nonetheless, "coupled" is also used to mean that two or more tangible components and/or the like are not necessarily tangibly in direct physical contact, but are able to co-operate, liaise, and/or interact, such as, for example, by being "optically coupled." Likewise, the term "coupled" is also understood to mean indirectly connected. It is further noted, in the context of the present patent application, since memory, such as a memory component and/or memory states, is intended to be non-transitory, the term physical, at least if used in relation to memory necessarily implies that such memory components and/or memory states, continuing with the example, are tangible.

Unless otherwise indicated, in the context of the present patent application, the term "or" if used to associate a list, such as A, B, or C, is intended to mean A, B, and C, here used in the inclusive sense, as well as A, B, or C, here used in the exclusive sense. With this understanding, "and" is used in the inclusive sense and intended to mean A, B, and C; whereas "and/or" can be used in an abundance of caution to make clear that all of the foregoing meanings are intended, although such usage is not required. In addition, the term "one or more" and/or similar terms is used to describe any feature, structure, characteristic, and/or the like in the singular, "and/or" is also used to describe a plurality and/or some other combination of features, structures, characteristics, and/or the like. Likewise, the term "based on" and/or similar terms are understood as not necessarily intending to convey an exhaustive list of factors, but to allow for existence of additional factors not necessarily expressly described.

Furthermore, it is intended, for a situation that relates to implementation of claimed subject matter and is subject to testing, measurement, and/or specification regarding degree, that the particular situation be understood in the following manner. As an example, in a given situation, assume a value of a physical property is to be measured. If alternatively reasonable approaches to testing, measurement, and/or specification regarding degree, at least with respect to the property, continuing with the example, is reasonably likely to occur to one of ordinary skill, at least for implementation purposes, claimed subject matter is intended to cover those alternatively reasonable approaches unless otherwise expressly indicated. As an example, if a plot of measurements over a region is produced and implementation of claimed subject matter refers to employing a measurement of slope over the region, but a variety of reasonable and alternative techniques to estimate the slope over that region exist, claimed subject matter is intended to cover those reasonable alternative techniques unless otherwise expressly indicated.

To the extent claimed subject matter is related to one or more particular measurements, such as with regard to physical manifestations capable of being measured physically, such as, without limit, temperature, pressure, voltage, current, electromagnetic radiation, etc., it is believed that claimed subject matter does not fall with the abstract idea judicial exception to statutory subject matter. Rather, it is asserted, that physical measurements are not mental steps and, likewise, are not abstract ideas.

It is noted, nonetheless, that a typical measurement model employed is that one or more measurements may respectively comprise a sum of at least two components. Thus, for a given measurement, for example, one component may comprise a deterministic component, which in an ideal sense, may comprise a physical value (e.g., sought via one or more measurements), often in the form of one or more signals, signal samples and/or states, and one component may comprise a random component, which may have a variety of sources that may be challenging to quantify. At times, for example, lack of measurement precision may affect a given measurement. Thus, for claimed subject matter, a statistical or stochastic model may be used in addition to a deterministic model as an approach to identification and/or prediction regarding one or more measurement values that may relate to claimed subject matter.

For example, a relatively large number of measurements may be collected to better estimate a deterministic component. Likewise, if measurements vary, which may typically occur, it may be that some portion of a variance may be explained as a deterministic component, while some portion of a variance may be explained as a random component. Typically, it is desirable to have stochastic variance associated with measurements be relatively small, if feasible. That is, typically, it may be preferable to be able to account for a reasonable portion of measurement variation in a deterministic manner, rather than a stochastic matter as an aid to identification and/or predictability.

Along these lines, a variety of techniques have come into use so that one or more measurements may be processed to better estimate an underlying deterministic component, as well as to estimate potentially random components. These techniques, of course, may vary with details surrounding a given situation. Typically, however, more complex problems may involve use of more complex techniques. In this regard, as alluded to above, one or more measurements of physical manifestations may be modelled deterministically and/or stochastically. Employing a model permits collected measurements to potentially be identified and/or processed, and/or potentially permits estimation and/or prediction of an underlying deterministic component, for example, with respect to later measurements to be taken. A given estimate may not be a perfect estimate; however, in general, it is expected that on average one or more estimates may better reflect an underlying deterministic component, for example, if random components that may be included in one or more obtained measurements, are considered. Practically speaking, of course, it is desirable to be able to generate, such as through estimation approaches, a physically meaningful model of processes affecting measurements to be taken.

In some situations, however, as indicated, potential influences may be complex. Therefore, seeking to understand appropriate factors to consider may be particularly challenging. In such situations, it is, therefore, not unusual to employ heuristics with respect to generating one or more estimates. Heuristics refers to use of experience related approaches that may reflect realized processes and/or realized results, such as with respect to use of historical measurements, for example. Heuristics, for example, may be employed in situations where more analytical approaches may be overly complex and/or nearly intractable. Thus, regarding claimed subject matter, an innovative feature may include, in an example embodiment, heuristics that may be employed, for example, to estimate and/or predict one or more measurements.

It is further noted that the terms "type" and/or "like," if used, such as with a feature, structure, characteristic, and/or the like, using "optical" or "electrical" as simple examples, means at least partially of and/or relating to the feature, structure, characteristic, and/or the like in such a way that presence of minor variations, even variations that might otherwise not be considered fully consistent with the feature, structure, characteristic, and/or the like, do not in general prevent the feature, structure, characteristic, and/or the like from being of a "type" and/or being "like," (such as being an "optical-type" or being "optical-like," for example) if the minor variations are sufficiently minor so that the feature, structure, characteristic, and/or the like would still be considered to be substantially present with such variations also present. Thus, continuing with this example, the terms optical-type and/or optical-like properties are necessarily intended to include optical properties. Likewise, the terms electrical-type and/or electrical-like properties, as another example, are necessarily intended to include electrical properties. It should be noted that the specification of the present patent application merely provides one or more illustrative examples and claimed subject matter is intended to not be limited to one or more illustrative examples; however, again, as has always been the case with respect to the specification of a patent application, particular context of description and/or usage provides helpful guidance regarding reasonable inferences to be drawn.

With advances in technology, it has become more typical to employ distributed computing and/or communication approaches in which portions of a process, such as signal processing of signal samples, for example, may be allocated among various devices, including one or more client devices and/or one or more server devices, via a computing and/or communications network, for example. A network may comprise two or more devices, such as network devices and/or computing devices, and/or may couple devices, such as network devices and/or computing devices, so that signal communications, such as in the form of signal packets and/or signal frames (e.g., comprising one or more signal samples), for example, may be exchanged, such as between a server device and/or a client device, as well as other types of devices, including between wired and/or wireless devices coupled via a wired and/or wireless network, for example.

In the context of the present patent application, the term network device refers to any device capable of communicating via and/or as part of a network and may comprise a computing device. While network devices may be capable of communicating signals (e.g., signal packets and/or frames), such as via a wired and/or wireless network, they may also be capable of performing operations associated with a computing device, such as arithmetic and/or logic operations, processing and/or storing operations (e.g., storing signal samples), such as in memory as tangible, physical memory states, and/or may, for example, operate as a server device and/or a client device in various embodiments. Network devices capable of operating as a server device, a client device and/or otherwise, may include, as examples, dedicated rack-mounted servers, desktop computers, laptop computers, set top boxes, tablets, netbooks, smart phones, wearable devices, integrated devices combining two or more features of the foregoing devices, and/or the like, or any combination thereof. As mentioned, signal packets and/or frames, for example, may be exchanged, such as between a server device and/or a client device, as well as other types of devices, including between wired and/or wireless devices coupled via a wired and/or wireless network, for example, or any combination thereof. It is noted that the terms, server, server device, server computing device, server computing platform and/or similar terms are used interchangeably. Similarly, the terms client, client device, client computing device, client computing platform and/or similar terms are also used interchangeably. While in some instances, for ease of description, these terms may be used in the singular, such as by referring to a "client device" or a "server device," the description is intended to encompass one or more client devices and/or one or more server devices, as appropriate. Along similar lines, references to a "database" are understood to mean, one or more databases and/or portions thereof, as appropriate.

It should be understood that for ease of description, a network device (also referred to as a networking device) may be embodied and/or described in terms of a computing device and vice-versa. However, it should further be understood that this description should in no way be construed so that claimed subject matter is limited to one embodiment, such as only a computing device and/or only a network device, but, instead, may be embodied as a variety of devices or combinations thereof, including, for example, one or more illustrative examples.

A network may also include now known, and/or to be later developed arrangements, derivatives, and/or improvements, including, for example, past, present and/or future mass storage, such as network attached storage (NAS), a storage area network (SAN), and/or other forms of device readable media, for example. A network may include a portion of the Internet, one or more local area networks (LANs), one or more wide area networks (WANs), wire-line type connections, wireless type connections, other connections, or any combination thereof. Thus, a network may be worldwide in scope and/or extent. Likewise, sub-networks, such as may employ differing architectures and/or may be substantially compliant and/or substantially compatible with differing protocols, such as network computing and/or communications protocols (e.g., network protocols), may interoperate within a larger network.

In the context of the present patent application, the term sub-network and/or similar terms, if used, for example, with respect to a network, refers to the network and/or a part thereof. Sub-networks may also comprise links, such as physical links, connecting and/or coupling nodes, so as to be capable to communicate signal packets and/or frames between devices of particular nodes, including via wired links, wireless links, or combinations thereof. Various types of devices, such as network devices and/or computing devices, may be made available so that device interoperability is enabled and/or, in at least some instances, may be transparent. In the context of the present patent application, the term "transparent," if used with respect to devices of a network, refers to devices communicating via the network in which the devices are able to communicate via one or more intermediate devices, such as one or more intermediate nodes, but without the communicating devices necessarily specifying the one or more intermediate nodes and/or the one or more intermediate devices of the one or more intermediate nodes and/or, thus, may include within the network the devices communicating via the one or more intermediate nodes and/or the one or more intermediate devices of the one or more intermediate nodes, but may engage in signal communications as if such intermediate nodes and/or intermediate devices are not necessarily involved. For example, a router may provide a link and/or connection between otherwise separate and/or independent LANs.

In the context of the present patent application, a "private network" refers to a particular, limited set of devices, such as network devices and/or computing devices, able to communicate with other devices, such as network devices and/or computing devices, in the particular, limited set, such as via signal packet and/or signal frame communications, for example, without a need for re-routing and/or redirecting signal communications. A private network may comprise a stand-alone network; however, a private network may also comprise a subset of a larger network, such as, for example, without limitation, all or a portion of the Internet. Thus, for example, a private network "in the cloud" may refer to a private network that comprises a subset of the Internet. Although signal packet and/or frame communications (e.g. signal communications) may employ intermediate devices of intermediate nodes to exchange signal packets and/or signal frames, those intermediate devices may not necessarily be included in the private network by not being a source or designated destination for one or more signal packets and/or signal frames, for example. It is understood in the context of the present patent application that a private network may direct outgoing signal communications to devices not in the private network, but devices outside the private network may not necessarily be able to direct inbound signal communications to devices included in the private network.

The Internet refers to a decentralized global network of interoperable networks that comply with the Internet Protocol (IP). It is noted that there are several versions of the Internet Protocol. The term Internet Protocol, IP, and/or similar terms are intended to refer to any version, now known and/or to be later developed. The Internet includes local area networks (LANs), wide area networks (WANs), wireless networks, and/or long haul public networks that, for example, may allow signal packets and/or frames to be communicated between LANs. The term World Wide Web (WWW or Web) and/or similar terms may also be used, although it refers to a part of the Internet that complies with the Hypertext Transfer Protocol (HTTP). For example, network devices may engage in an HTTP session through an exchange of appropriately substantially compatible and/or substantially compliant signal packets and/or frames. It is noted that there are several versions of the Hypertext Transfer Protocol. The term Hypertext Transfer Protocol, HTTP, and/or similar terms are intended to refer to any version, now known and/or to be later developed. It is likewise noted that in various places in this document substitution of the term Internet with the term World Wide Web ("Web") may be made without a significant departure in meaning and may, therefore, also be understood in that manner if the statement would remain correct with such a substitution.

The term electronic file and/or the term electronic document are used throughout this document to refer to a set of stored memory states and/or a set of physical signals associated in a manner so as to thereby at least logically form a file (e.g., electronic) and/or an electronic document. That is, it is not meant to implicitly reference a particular syntax, format and/or approach used, for example, with respect to a set of associated memory states and/or a set of associated physical signals. If a particular type of file storage format and/or syntax, for example, is intended, it is referenced expressly. It is further noted an association of memory states, for example, may be in a logical sense and not necessarily in a tangible, physical sense. Thus, although signal and/or state components of a file and/or an electronic document, for example, are to be associated logically, storage thereof, for example, may reside in one or more different places in a tangible, physical memory, in an embodiment.

A Hyper Text Markup Language ("HTML"), for example, may be utilized to specify digital content and/or to specify a format thereof, such as in the form of an electronic file and/or an electronic document, such as a Web page, Web site, etc., for example. An Extensible Markup Language ("XML") may also be utilized to specify digital content and/or to specify a format thereof, such as in the form of an electronic file and/or an electronic document, such as a Web page, Web site, etc., in an embodiment. Of course, HTML and/or XML are merely examples of "markup" languages, provided as non-limiting illustrations. Furthermore, HTML and/or XML are intended to refer to any version, now known and/or to be later developed, of these languages. Likewise, claimed subject matter are not intended to be limited to examples provided as illustrations, of course.

In the context of the present patent application, the terms "entry," "electronic entry," "document," "electronic document," "content", "digital content," "item," and/or similar terms are meant to refer to signals and/or states in a physical format, such as a digital signal and/or digital state format, e.g., that may be perceived by a user if displayed, played, tactilely generated, etc. and/or otherwise executed by a device, such as a digital device, including, for example, a computing device, but otherwise might not necessarily be readily perceivable by humans (e.g., if in a digital format). Likewise, in the context of the present patent application, digital content provided to a user in a form so that the user is able to readily perceive the underlying content itself (e.g., content presented in a form consumable by a human, such as hearing audio, feeling tactile sensations and/or seeing images, as examples) is referred to, with respect to the user, as "consuming" digital content, "consumption" of digital content, "consumable" digital content and/or similar terms. For one or more embodiments, an electronic document and/or an electronic file may comprise a Web page of code (e.g., computer instructions) in a markup language executed or to be executed by a computing and/or networking device, for example. In another embodiment, an electronic document and/or electronic file may comprise a portion and/or a region of a Web page. However, claimed subject matter is not intended to be limited in these respects.

Also, for one or more embodiments, an electronic document and/or electronic file may comprise a number of components. As previously indicated, in the context of the present patent application, a component is physical, but is not necessarily tangible. As an example, components with reference to an electronic document and/or electronic file, in one or more embodiments, may comprise text, for example, in the form of physical signals and/or physical states (e.g., capable of being physically displayed). Typically, memory states, for example, comprise tangible components, whereas physical signals are not necessarily tangible, although signals may become (e.g., be made) tangible, such as if appearing on a tangible display, for example, as is not uncommon. Also, for one or more embodiments, components with reference to an electronic document and/or electronic file may comprise a graphical object, such as, for example, an image, such as a digital image, and/or subobjects, including attributes thereof, which, again, comprise physical signals and/or physical states (e.g., capable of being tangibly displayed). In an embodiment, digital content may comprise, for example, text, images, audio, video, and/or other types of electronic documents and/or electronic files, including portions thereof, for example.

Also, in the context of the present patent application, the term "parameters" (e.g., one or more parameters), "values" (e.g., one or more values), "symbols" (e.g., one or more symbols) "bits" (e.g., one or more bits), "elements" (e.g., one or more elements), "characters" (e.g., one or more characters), "numbers" (e.g., one or more numbers), "numerals" (e.g., one or more numerals) or "measurements" (e.g., one or more measurements) refer to material descriptive of a collection of signals, such as in one or more electronic documents and/or electronic files, and exist in the form of physical signals and/or physical states, such as memory states. For example, one or more parameters, values, symbols, bits, elements, characters, numbers, numerals or measurements, such as referring to one or more aspects of an electronic document and/or an electronic file comprising an image, may include, as examples, time of day at which an image was captured, latitude and longitude of an image capture device, such as a camera, for example, etc. In another example, one or more parameters, values, symbols, bits, elements, characters, numbers, numerals or measurements, relevant to digital content, such as digital content comprising a technical article, as an example, may include one or more authors, for example. Claimed subject matter is intended to embrace meaningful, descriptive parameters, values, symbols, bits, elements, characters, numbers, numerals or measurements in any format, so long as the one or more parameters, values, symbols, bits, elements, characters, numbers, numerals or measurements comprise physical signals and/or states, which may include, as parameter, value, symbol bits, elements, characters, numbers, numerals or measurements examples, collection name (e.g., electronic file and/or electronic document identifier name), technique of creation, purpose of creation, time and date of creation, logical path if stored, coding formats (e.g., type of computer instructions, such as a markup language) and/or standards and/or specifications used so as to be protocol compliant (e.g., meaning substantially compliant and/or substantially compatible) for one or more uses, and so forth.

Signal packet communications and/or signal frame communications, also referred to as signal packet transmissions and/or signal frame transmissions (or merely "signal packets" or "signal frames"), may be communicated between nodes of a network, where a node may comprise one or more network devices and/or one or more computing devices, for example. As an illustrative example, but without limitation, a node may comprise one or more sites employing a local network address, such as in a local network address space. Likewise, a device, such as a network device and/or a computing device, may be associated with that node. It is also noted that in the context of this patent application, the term "transmission" is intended as another term for a type of signal communication that may occur in any one of a variety of situations. Thus, it is not intended to imply a particular directionality of communication and/or a particular initiating end of a communication path for the "transmission" communication. For example, the mere use of the term in and of itself is not intended, in the context of the present patent application, to have particular implications with respect to the one or more signals being communicated, such as, for example, whether the signals are being communicated "to" a particular device, whether the signals are being communicated "from" a particular device, and/or regarding which end of a communication path may be initiating communication, such as, for example, in a "push type" of signal transfer or in a "pull type" of signal transfer. In the context of the present patent application, push and/or pull type signal transfers are distinguished by which end of a communications path initiates signal transfer.

Thus, a signal packet and/or frame may, as an example, be communicated via a communication channel and/or a communication path, such as comprising a portion of the Internet and/or the Web, from a site via an access node coupled to the Internet or vice-versa. Likewise, a signal packet and/or frame may be forwarded via network nodes to a target site coupled to a local network, for example. A signal packet and/or frame communicated via the Internet and/or the Web, for example, may be routed via a path, such as either being "pushed" or "pulled," comprising one or more gateways, servers, etc. that may, for example, route a signal packet and/or frame, such as, for example, substantially in accordance with a target and/or destination address and availability of a network path of network nodes to the target and/or destination address. Although the Internet and/or the Web comprise a network of interoperable networks, not all of those interoperable networks are necessarily available and/or accessible to the public.

In the context of the particular patent application, a network protocol, such as for communicating between devices of a network, may be characterized, at least in part, substantially in accordance with a layered description, such as the so-called Open Systems Interconnection (OSI) seven layer type of approach and/or description. A network computing and/or communications protocol (also referred to as a network protocol) refers to a set of signaling conventions, such as for communication transmissions, for example, as may take place between and/or among devices in a network. In the context of the present patent application, the term "between" and/or similar terms are understood to include "among" if appropriate for the particular usage and vice-versa. Likewise, in the context of the present patent application, the terms "compatible with," "comply with" and/or similar terms are understood to respectively include substantial compatibility and/or substantial compliance.

A network protocol, such as protocols characterized substantially in accordance with the aforementioned OSI description, has several layers. These layers are referred to as a network stack. Various types of communications (e.g., transmissions), such as network communications, may occur across various layers. A lowest level layer in a network stack, such as the so-called physical layer, may characterize how symbols (e.g., bits and/or bytes) are communicated as one or more signals (and/or signal samples) via a physical medium (e.g., twisted pair copper wire, coaxial cable, fiber optic cable, wireless air interface, combinations thereof, etc.). Progressing to higher-level layers in a network protocol stack, additional operations and/or features may be available via engaging in communications that are substantially compatible and/or substantially compliant with a particular network protocol at these higher-level layers. For example, higher-level layers of a network protocol may, for example, affect device permissions, user permissions, etc.

A network and/or sub-network, in an embodiment, may communicate via signal packets and/or signal frames, such via participating digital devices and may be substantially compliant and/or substantially compatible with, but is not limited to, now known and/or to be developed, versions of any of the following network protocol stacks: ARCNET, AppleTalk, ATM, Bluetooth, DECnet, Ethernet, FDDI, Frame Relay, HIPPI, IEEE 1394, IEEE 802.11, IEEE-488, Internet Protocol Suite, IPX, Myrinet, OSI Protocol Suite, QsNet, RS-232, SPX, System Network Architecture, Token Ring, USB, and/or X.25. A network and/or sub-network may employ, for example, a version, now known and/or later to be developed, of the following: TCP/IP, UDP, DECnet, NetBEUI, IPX, AppleTalk and/or the like. Versions of the Internet Protocol (IP) may include IPv4, IPv6, and/or other later to be developed versions.

Regarding aspects related to a network, including a communications and/or computing network, a wireless network may couple devices, including client devices, with the network. A wireless network may employ stand-alone, ad-hoc networks, mesh networks, Wireless LAN (WLAN)

networks, cellular networks, and/or the like. A wireless network may further include a system of terminals, gateways, routers, and/or the like coupled by wireless radio links, and/or the like, which may move freely, randomly and/or organize themselves arbitrarily, such that network topology may change, at times even rapidly. A wireless network may further employ a plurality of network access technologies, including a version of Long Term Evolution (LTE), WLAN, Wireless Router (WR) mesh, 2nd, 3rd, or 4th generation (2G, 3G, or 4G) cellular technology and/or the like, whether currently known and/or to be later developed. Network access technologies may enable wide area coverage for devices, such as computing devices and/or network devices, with varying degrees of mobility, for example.

A network may enable radio frequency and/or other wireless type communications via a wireless network access technology and/or air interface, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, ultra-wideband (UWB), 802.11b/g/n, and/or the like. A wireless network may include virtually any type of now known and/or to be developed wireless communication mechanism and/or wireless communications protocol by which signals may be communicated between devices, between networks, within a network, and/or the like, including the foregoing, of course.

Figure 5:
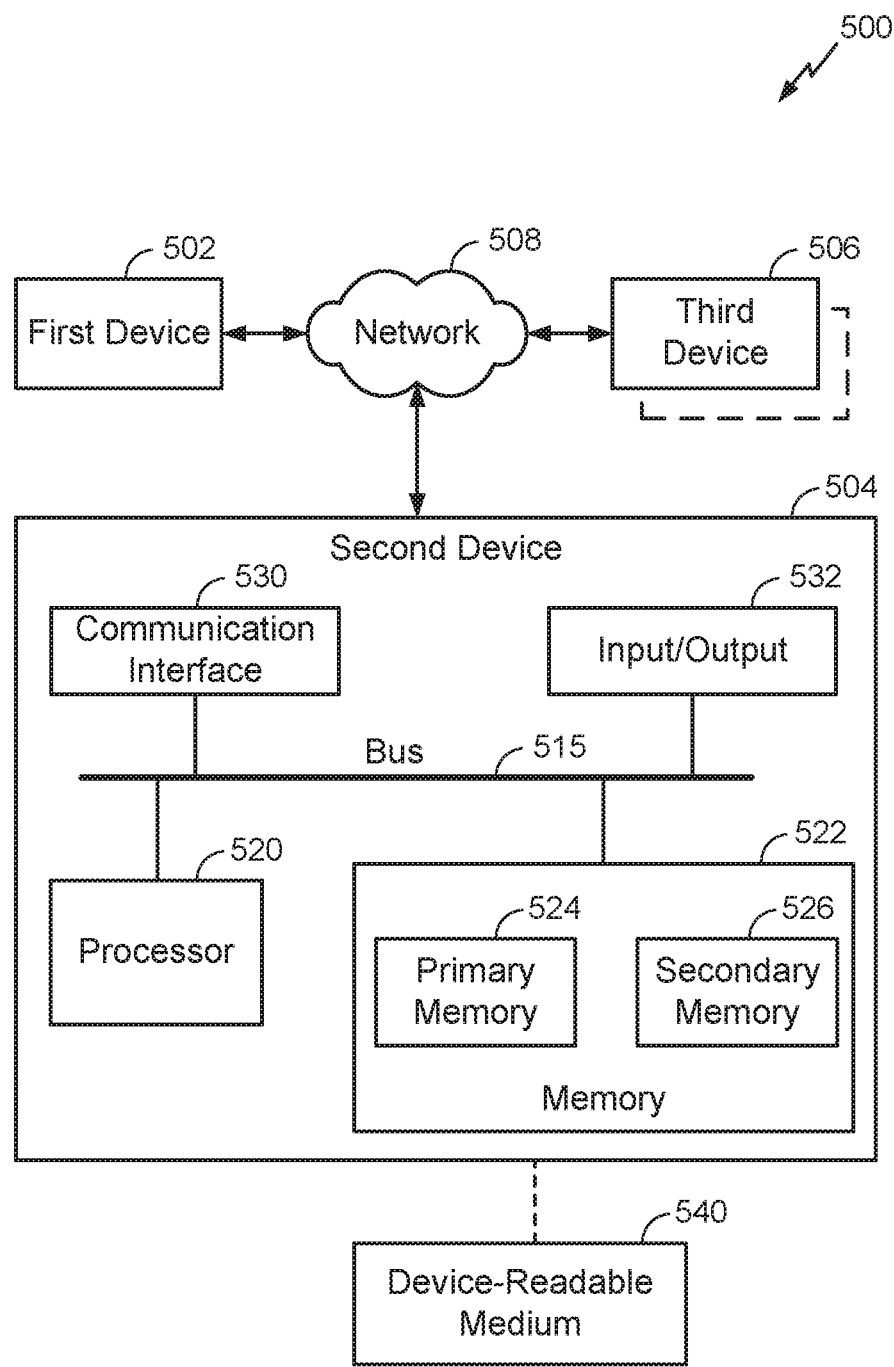
FIG. 5 is a schematic diagram illustrating an implementation of an example computing environment associated with an authentication engine.

In one example embodiment, as shown in FIG. 5, a system embodiment may comprise a local network (e.g., device 504 and medium 540) and/or another type of network, such as a computing and/or communications network. For purposes of illustration, therefore, FIG. 5 shows an embodiment 500 of a system that may be employed to implement either type or both types of networks. Network 508 may comprise one or more network connections, links, processes, services, applications, and/or resources to facilitate and/or support communications, such as an exchange of communication signals, for example, between a computing device, such as 502, and another computing device, such as 506, which may, for example, comprise one or more client computing devices and/or one or more server computing device. By way of example, but not limitation, network 508 may comprise wireless and/or wired communication links, telephone and/or telecommunications systems, Wi-Fi networks, Wi-MAX networks, the Internet, a local area network (LAN), a wide area network (WAN), or any combinations thereof.

Example devices in FIG. 5 may comprise features, for example, of a client computing device and/or a server computing device, in an embodiment. It is further noted that the term computing device, in general, whether employed as a client and/or as a server, or otherwise, refers at least to a processor and a memory connected by a communication bus. Likewise, in the context of the present patent application at least, this is understood to refer to sufficient structure within the meaning of 35 USC § 112 (f) so that it is specifically intended that 35 USC § 112 (f) not be implicated by use of the term "computing device" and/or similar terms; however, if it is determined, for some reason not immediately apparent, that the foregoing understanding cannot stand and that 35 USC § 112 (f), therefore, necessarily is implicated by the use of the term "computing device" and/or similar terms, then, it is intended, pursuant to that statutory section, that corresponding structure, material and/or acts for performing one or more functions be understood and be interpreted to be described at least in FIGS. 3 and 4 and in the text associated with the foregoing figure(s) of the present patent application.

Referring now to FIG. 5, in an embodiment, first and third devices 502 and 506 may be capable of rendering a graphical user interface (GUI) for a network device and/or a computing device, for example, so that a user-operator may engage in system use. Device 504 may potentially serve a similar function in this illustration. Likewise, in FIG. 5, computing device 502 ('first device' in figure) may interface with computing device 504 ('second device' in figure), which may, for example, also comprise features of a client computing device and/or a server computing device, in an embodiment. Processor (e.g., processing device) 520 and memory 522, which may comprise primary memory 524 and secondary memory 526, may communicate by way of a communication bus 515, for example. The term "computing device," in the context of the present patent application, refers to a system and/or a device, such as a computing apparatus, that includes a capability to process (e.g., perform computations) and/or store digital content, such as electronic files, electronic documents, measurements, text, images, video, audio, etc. in the form of signals and/or states. Thus, a computing device, in the context of the present patent application, may comprise hardware, software, firmware, or any combination thereof (other than software per se). Computing device 504, as depicted in FIG. 5, is merely one example, and claimed subject matter is not limited in scope to this particular example.

For one or more embodiments, a device, such as a computing device and/or networking device, may comprise, for example, any of a wide range of digital electronic devices, including, but not limited to, desktop and/or notebook computers, high-definition televisions, digital versatile disc (DVD) and/or other optical disc players and/or recorders, game consoles, satellite television receivers, cellular telephones, tablet devices, wearable devices, personal digital assistants, mobile audio and/or video playback and/or recording devices, Internet of Things (IOT) type devices, or any combination of the foregoing. Further, unless specifically stated otherwise, a process as described, such as with reference to flow diagrams and/or otherwise, may also be executed and/or affected, in whole or in part, by a computing device and/or a network device. A device, such as a computing device and/or network device, may vary in terms of capabilities and/or features. Claimed subject matter is intended to cover a wide range of potential variations. For example, a device may include a numeric keypad and/or other display of limited functionality, such as a monochrome liquid crystal display (LCD) for displaying text, for example. In contrast, however, as another example, a web-enabled device may include a physical and/or a virtual keyboard, mass storage, one or more accelerometers, one or more gyroscopes, global positioning system (GPS) and/or other location-identifying type capability, and/or a display with a higher degree of functionality, such as a touch-sensitive color 5D or 3D display, for example.

As suggested previously, communications between a computing device and/or a network device and a wireless network may be in accordance with known and/or to be developed network protocols including, for example, global system for mobile communications (GSM), enhanced data rate for GSM evolution (EDGE), 802.11b/g/n/h, etc., and/or worldwide interoperability for microwave access (WiMAX). A computing device and/or a networking device may also have a subscriber identity module (SIM) card, which, for example, may comprise a detachable or embedded smart card that is able to store subscription content of a user, and/or is also able to store a contact list. It is noted, however, that a SIM card may also be electronic, meaning that is may simply be stored in a particular location in memory of the computing and/or networking device. A user may own the computing device and/or network device or may otherwise be a user, such as a primary user, for example. A device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a computing and/or communications network may be embodied as a wired network, wireless network, or any combinations thereof.

A computing and/or network device may include and/or may execute a variety of now known and/or to be developed operating systems, derivatives and/or versions thereof, including computer operating systems, such as Windows, iOS, Linux, a mobile operating system, such as iOS, Android, Windows Mobile, and/or the like. A computing device and/or network device may include and/or may execute a variety of possible applications, such as a client software application enabling communication with other devices. For example, one or more messages (e.g., content) may be communicated, such as via one or more protocols, now known and/or later to be developed, suitable for communication of email, short message service (SMS), and/or multimedia message service (MMS), including via a network, such as a social network, formed at least in part by a portion of a computing and/or communications network, including, but not limited to, Facebook, LinkedIn, Twitter, Flickr, and/or Google+, to provide only a few examples. A computing and/or network device may also include executable computer instructions to process and/or communicate digital content, such as, for example, textual content, digital multimedia content, and/or the like. A computing and/or network device may also include executable computer instructions to perform a variety of possible tasks, such as browsing, searching, playing various forms of digital content, including locally stored and/or streamed video, and/or games such as, but not limited to, fantasy sports leagues. The foregoing is provided merely to illustrate that claimed subject matter is intended to include a wide range of possible features and/or capabilities.

In FIG. 5, computing device 502 may provide one or more sources of executable computer instructions in the form physical states and/or signals (e.g., stored in memory states), for example. Computing device 502 may communicate with computing device 504 by way of a network connection, such as via network 508, for example. As previously mentioned, a connection, while physical, may not necessarily be tangible. Although computing device 504 of FIG. 5 shows various tangible, physical components, claimed subject matter is not limited to a computing devices having only these tangible components as other implementations and/or embodiments may include alternative arrangements that may comprise additional tangible components or fewer tangible components, for example, that function differently while achieving similar results. Rather, examples are provided merely as illustrations. It is not intended that claimed subject matter be limited in scope to illustrative examples.

Memory 522 may comprise any non-transitory storage mechanism. Memory 522 may comprise, for example, primary memory 524 and secondary memory 526, additional memory circuits, mechanisms, or combinations thereof may be used. Memory 522 may comprise, for example, random access memory, read only memory, etc., such as in the form of one or more storage devices and/or systems, such as, for example, a disk drive including an optical disc drive, a tape drive, a solid-state memory drive, etc., just to name a few examples.

Memory 522 may be utilized to store a program of executable computer instructions. For example, processor 520 may fetch executable instructions from memory and proceed to execute the fetched instructions. Memory 522 may also comprise a memory controller for accessing device readable-medium 540 that may carry and/or make accessible digital content, which may include code, and/or instructions, for example, executable by processor 520 and/or some other device, such as a controller, as one example, capable of executing computer instructions, for example. Under direction of processor 520, a non-transitory memory, such as memory cells storing physical states (e.g., memory states), comprising, for example, a program of executable computer instructions, may be executed by processor 520 and able to generate signals to be communicated via a network, for example, as previously described. Generated signals may also be stored in memory, also previously suggested.

Memory 522 may store electronic files and/or electronic documents, such as relating to one or more users, and may also comprise a computer-readable medium that may carry and/or make accessible content, including code and/or instructions, for example, executable by processor 520 and/or some other device, such as a controller, as one example, capable of executing computer instructions, for example. As previously mentioned, the term electronic file and/or the term electronic document are used throughout this document to refer to a set of stored memory states and/or a set of physical signals associated in a manner so as to thereby form an electronic file and/or an electronic document. That is, it is not meant to implicitly reference a particular syntax, format and/or approach used, for example, with respect to a set of associated memory states and/or a set of associated physical signals. It is further noted an association of memory states, for example, may be in a logical sense and not necessarily in a tangible, physical sense. Thus, although signal and/or state components of an electronic file and/or electronic document, are to be associated logically, storage thereof, for example, may reside in one or more different places in a tangible, physical memory, in an embodiment.

Algorithmic descriptions and/or symbolic representations are examples of techniques used by those of ordinary skill in the signal processing and/or related arts to convey the substance of their work to others skilled in the art. An algorithm is, in the context of the present patent application, and generally, is considered to be a self-consistent sequence of operations and/or similar signal processing leading to a desired result. In the context of the present patent application, operations and/or processing involve physical manipulation of physical quantities. Typically, although not necessarily, such quantities may take the form of electrical and/or magnetic signals and/or states capable of being stored, transferred, combined, compared, processed and/or otherwise manipulated, for example, as electronic signals and/or states making up components of various forms of digital content, such as signal measurements, text, images, video, audio, etc.

It has proven convenient at times, principally for reasons of common usage, to refer to such physical signals and/or physical states as bits, values, elements, parameters, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically in the form of physical electronic and/or magnetic quantities, within memories, registers, and/or other storage devices, processing devices, and/or display devices of the special purpose computer and/or similar special purpose computing and/or network device. In the context of this particular patent application, as mentioned, the term "specific apparatus" therefore includes a general purpose computing and/or network device, such as a general purpose computer, once it is programmed to perform particular functions, such as pursuant to program software instructions.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and/or storage of charge or a release of stored charge. Likewise, in other memory devices, a change of state may comprise a physical change, such as a transformation in magnetic orientation. Likewise, a physical change may comprise a transformation in molecular structure, such as from crystalline form to amorphous form or vice-versa. In still other memory devices, a change in physical state may involve quantum mechanical phenomena, such as, superposition, entanglement, and/or the like, which may involve quantum bits (qubits), for example. The foregoing is not intended to be an exhaustive list of all examples in which a change in state from a binary one to a binary zero or vice-versa in a memory device may comprise a transformation, such as a physical, but non-transitory, transformation. Rather, the foregoing is intended as illustrative examples.

Referring again to FIG. 5, processor 520 may comprise one or more circuits, such as digital circuits, to perform at least a portion of a computing procedure and/or process. By way of example, but not limitation, processor 520 may comprise one or more processors, such as controllers, microprocessors, microcontrollers, application specific integrated circuits, digital signal processors, programmable logic devices, field programmable gate arrays, the like, or any combination thereof. In various implementations and/or embodiments, processor 520 may perform signal processing, typically substantially in accordance with fetched executable computer instructions, such as to manipulate signals and/or states, to construct signals and/or states, etc., with signals and/or states generated in such a manner to be communicated and/or stored in memory, for example.

FIG. 5 also illustrates device 504 as including a component 532 operable with input/output devices, for example, so that signals and/or states may be appropriately communicated between devices, such as device 504 and an input device and/or device 504 and an output device. A user may make use of an input device, such as a computer mouse, stylus, track ball, keyboard, and/or any other similar device capable of receiving user actions and/or motions as input signals. Likewise, for a device having speech to text capability, a user may speak to a device to generate input signals. A user may make use of an output device, such as a display, a printer, etc., and/or any other device capable of providing signals and/or generating stimuli for a user, such as visual stimuli, audio stimuli and/or other similar stimuli.

In the preceding description, various aspects of claimed subject matter have been described. For purposes of explanation, specifics, such as amounts, systems and/or configurations, as examples, were set forth. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all modifications and/or changes as fall within claimed subject matter.

What is claimed is:

1. A method comprising:
    generating a first signal to apply a first sensory stimulus to a human subject, the first sensory stimulus being generated external to the human subject to evoke a particular involuntary response by a particular unique individual;
    generating a second signal to apply a second sensory stimulus to the human subject, the second sensory stimulus being temporally correlated with the first sensory stimulus;
    inferring that a third signal, the third signal comprising a voltage and/or current being generated by one or more first sensors adapted to be in contact with a body of the human subject, indicates the particular involuntary response to the first sensory stimulus by the particular unique individual; and
    authenticating an identity of the human subject as being an identity of the particular unique individual based, at least in part, on a detected temporal correlation of the third signal and a fourth signal, the fourth signal comprising a voltage and/or current being generated by one or more second sensors adapted to be in contact with the body of the human subject, indicating an involuntary response to the second sensory stimulus, the detected temporal correlation to comprise a lead or lag of the third signal with respect to the fourth signal computed by a processor based, at least in part, on the voltage and/or current of the third signal and the voltage and/or current of the fourth signal.

2. The method of claim 1, wherein at least one of the one or more the first sensors is positioned on a scalp of the human subject to generate the third signal responsive to one or more brain signals generated by the human subject.

3. The method of claim 2, wherein inferring that the third signal indicates the particular involuntary response to the first sensory stimulus by the particular unique individual further comprises classifying at least one of the one or more brain signals generated by the human subject as a P300 brain signal.

4. The method of claim 1, wherein the second sensory stimulus comprises at least one first frequency characteristic, and wherein the fourth signal is generated by at least one of the one or more second sensors responsive to a steady-state visual evoked potential (SSVEP) signal having at least one second frequency characteristic, the at least one second frequency characteristic being based, at least in part, on the at least one first frequency characteristic.

5. The method of claim 4, and further comprising detecting the temporal correlation of the third signal and the fourth signal based, at least in part, on temporal correlation of the third signal with the at least one second frequency characteristic and a variation in amplitude in the fourth signal.

6. The method of claim 1, wherein the first and second sensory stimuli comprise images.

7. The method of claim 1, wherein generating the first signal to apply the first sensory stimulus to the human subject further comprises presenting at least one visual image of particular significance to the particular unique individual temporally interleaved with presentation of one or more images which are not of particular significance to the particular unique individual.

8. The method of claim 7, wherein the at least one visual image of particular significance to the particular unique individual is to evoke a P300 brain signal in the particular unique individual.

9. The method of claim 1, and further comprising detecting the temporal correlation of the third signal and the fourth signal based, at least in part, on difference between a time of detection of a characteristic of the third signal and detection of a time of detection of a characteristic of the fourth signal.

10. The method of claim 1, wherein generating the first signal to apply the first sensory stimulus to the human subject further comprises generating at least one sound of particular significance to the particular unique individual temporally interleaved with at least one sound that is not of particular significance to the particular unique individual.

11. The method of claim 1, wherein the first sensory stimulus comprises application of pressure at known locations of a scalp of the human subject.

12. The method of claim 1, wherein generating the first signal to apply a first sensory stimulus to the human subject further comprises:
fetching an electronic document associated with the identity of the particular unique individual from a non-transitory device-readable memory; and
executing device readable instructions by a computing device to generate control and/or content signals based, at least in part, on the fetched electronic document.

13. The method of claim 1, wherein the detected temporal correlation is based, at least in part, on an expected lag between the particular involuntary response to the first sensory stimulus and the involuntary response to the second sensory stimulus.

14. An apparatus comprising:
one or more processors to generate a first signal to apply a first sensory stimulus to a human subject, the first sensory stimulus to evoke a particular involuntary response by a particular unique individual, and to generate a second signal to apply a second sensory stimulus to the human subject, the second sensory stimulus being temporally correlated with the first sensory stimulus;
one or more first sensors, the one or more first sensors adapted to be in contact with a body of the human subject, to generate a third signal comprising a voltage and/or current responsive to a first involuntary response by the human subject to application of the first sensory stimulus; and
one or more second sensors, the one or more second sensors to be adapted to be in contact with the body of the human subject, to generate a fourth signal comprising a voltage and/or current responsive to a second involuntary response by the human subject to application of the second sensory stimulus,
wherein the one or more processors are further to:
infer that the third signal indicates the particular involuntary response to the first sensory stimulus by the particular unique individual; and
authenticate an identity of the human subject as being an identity of the particular unique individual based, at least in part, on a detected temporal correlation of the third signal and the fourth signal indicating an involuntary response to the second sensory stimulus, the detected temporal correlation to comprise a lead or lag of the third signal with respect to the fourth signal computed by the one or more processors based, at least in part, on the voltage and/or current of the third signal and the voltage and/or current of the fourth signal.

15. The apparatus of claim 14, wherein the one or more processors are further to:
fetch an electronic document associated with the identity of the particular unique individual from a non-transitory device-readable memory; and
execute device readable instructions to generate the first signal as control and/or content signals based, at least in part, on the fetched electronic document.

16. The apparatus of claim 14, wherein the one or more processors are further to:
determine the detected temporal correlation of the third signal and the fourth signal based, at least in part, on an expected time difference between detection of an event in third signal and detection of an event in the fourth signal, the expected time difference being obtained from the fetched electronic document.

17. The apparatus of claim 14, wherein the one or more processors are further to infer that the third signal indicates the particular involuntary response to the first sensory stimulus by the particular unique individual based, at least in part, on a classification of at least one brain signal as a P300 brain signal.

18. The apparatus of claim 14, wherein the second sensory stimulus comprises at least one first frequency characteristic, and wherein the fourth signal to be generated by at least one of the one or more second sensors responsive to a steady-state visual evoked potential (SSVEP) signal having at least one second frequency characteristic, the at least one second frequency characteristic being based, at least in part, on the at least one first frequency characteristic.

19. The apparatus of claim 18, wherein the one or more processors are further to detect the temporal correlation of the third signal and the fourth signal based, at least in part, on a temporal correlation of the third signal with the at least one second frequency characteristic and a variation in amplitude in the fourth signal.

20. An article comprising:
a non-transitory storage medium comprising device-readable instructions stored thereon that are executable by a processor to:
generate a first signal to apply a first sensory stimulus to a human subject, the first sensory stimulus to evoke a particular involuntary response by a particular unique individual;
generate a second signal to apply a second sensory stimulus to the human subject, the second sensory stimulus being temporally correlated with the first sensory stimulus;
infer that a third signal, the third signal comprising a voltage and/or signal to be generated by one or more first sensors adapted to be in contact with a body of the human subject, indicates the particular involuntary response to the first sensory stimulus by the particular unique individual; and authenticate an identity of the human subject as being an identity of the particular unique individual based, at least in part, on a detected temporal correlation of the third signal and a fourth signal, the fourth signal comprising a voltage and/or current to be generated by one or more second sensors adapted to be in contact with the body of the human subject, indicating an involuntary response to the second sensory stimulus, the detected temporal correlation to comprise a lead or lag of the third signal with respect to the fourth signal computed by the processor based, at least in part, on the voltage and/or current of the third signal and the voltage and/or current of the fourth signal.

\* \* \* \* \*